(12) United States Patent
Bohringer et al.

(10) Patent No.: US 9,975,109 B2
(45) Date of Patent: May 22, 2018

(54) CATALYST SYSTEM BASED ON SPHERICAL ACTIVATED CARBON AS A CARRIER AND USE THEREOF

(71) Applicants: Blucher GmbH, Erkrath (DE); Friedrich-Alexander-Universitat Erlangen-Nurnberg, Erlangen (DE)

(72) Inventors: Bertram Bohringer, Erkrath (DE); Sven Fichtner, Ekrath (DE); Christian Schrage, Ekrath (DE); Jann-Michael Giebelhausen, Erkrath (DE); Peter Wasserscheidt, Erlangen (DE); Bastian Etzold, Erlangen (DE); Heiko Klefer, Erlangen (DE)

(73) Assignee: Blücher GmbH, Erkrath (DE)

( * ) Notice: Subject to any disclaimer, the term of this patent is extended or adjusted under 35 U.S.C. 154(b) by 62 days.

(21) Appl. No.: 15/103,065

(22) PCT Filed: Nov. 25, 2014

(86) PCT No.: PCT/EP2014/003138
§ 371 (c)(1),
(2) Date: Jun. 9, 2016

(87) PCT Pub. No.: WO2015/086109
PCT Pub. Date: Jun. 18, 2015

(65) Prior Publication Data
US 2016/0296911 A1    Oct. 13, 2016

(30) Foreign Application Priority Data

Dec. 9, 2013  (DE) .................. 10 2013 020 233
Mar. 12, 2014 (DE) .................. 10 2014 103 351

(51) Int. Cl.
| | | |
|---|---|---|
| *C01B 31/08* | (2006.01) |
| *B01J 23/46* | (2006.01) |
| *B01J 37/18* | (2006.01) |
| *B01J 23/42* | (2006.01) |
| *B01J 23/44* | (2006.01) |
| *B01J 35/00* | (2006.01) |
| *B01J 37/02* | (2006.01) |
| *B01J 37/12* | (2006.01) |
| *B01J 20/20* | (2006.01) |
| *B01J 21/18* | (2006.01) |
| *B01J 23/40* | (2006.01) |
| *B01J 35/08* | (2006.01) |
| *B01J 20/28* | (2006.01) |
| *A62D 5/00* | (2006.01) |
| *B01J 20/30* | (2006.01) |
| *B01J 20/32* | (2006.01) |
| *B01J 20/02* | (2006.01) |
| *H01M 4/90* | (2006.01) |
| *C07C 29/141* | (2006.01) |
| *C07C 51/36* | (2006.01) |

(Continued)

(52) U.S. Cl.
CPC .............. *B01J 23/462* (2013.01); *A62D 5/00* (2013.01); *B01D 39/2058* (2013.01); *B01J 20/0225* (2013.01); *B01J 20/20* (2013.01); *B01J 20/28019* (2013.01); *B01J 20/28076* (2013.01); *B01J 20/3078* (2013.01); *B01J 20/3085* (2013.01); *B01J 20/3204* (2013.01); *B01J 20/3236* (2013.01); *B01J 20/3293* (2013.01); *B01J 21/18* (2013.01); *B01J 23/40* (2013.01); *B01J 23/42* (2013.01); *B01J 23/44* (2013.01); *B01J 35/0006* (2013.01); *B01J 35/0026* (2013.01); *B01J 35/0093* (2013.01); *B01J 35/08* (2013.01); *B01J 35/108* (2013.01); *B01J 35/1023* (2013.01); *B01J 35/1028* (2013.01); *B01J 35/1042* (2013.01); *B01J 35/1047* (2013.01); *B01J 35/1061* (2013.01); *B01J 37/0207* (2013.01); *B01J 37/0221* (2013.01); *B01J 37/12* (2013.01); *B01J 37/16* (2013.01); *B01J 37/18* (2013.01); *C07C 29/141* (2013.01); *C07C 51/36* (2013.01); *C07C 57/30* (2013.01); *H01M 4/9083* (2013.01); *A62D 9/00* (2013.01); *B01J 23/16* (2013.01); *B01J 23/48* (2013.01); *B01J 23/70* (2013.01); *B01J 35/023* (2013.01); *B01J 35/10* (2013.01); *C01B 32/354* (2017.08)

(58) Field of Classification Search
CPC ........................................................ B01J 20/20
See application file for complete search history.

(56) References Cited

U.S. PATENT DOCUMENTS

| | | | | |
|---|---|---|---|---|
| 3,891,708 A | * | 6/1975 | Woodrum ............. | C07C 213/10 564/497 |
| 5,110,779 A | * | 5/1992 | Hucul ...................... | B01J 23/40 502/185 |

(Continued)

FOREIGN PATENT DOCUMENTS

| | | |
|---|---|---|
| DE | 10137248 | 2/2003 |
| DE | 102005024845 | 11/2006 |

(Continued)

OTHER PUBLICATIONS

Auer et al: "Carbons as supports for industrial precious metal catalysts", Applied Catalysis A: General, Elsevier Science, Amsterdam, NL, vol. 173, No. 2, Oct. 25, 1998 (Oct. 25, 1998), pp. 259-271, XP0 0 4 2 7 1 52 5, ISSN : 0 9 2 6-8 6 0 X, D O I: 1 0 . 1 0 1 6 / S0926-860X(98)00184-7.

*Primary Examiner* — Stuart Hendrickson
(74) *Attorney, Agent, or Firm* — Edward E. Sowers; Brannon Sowers & Cracraft PC

(57) ABSTRACT

The invention relates to a method for producing a catalyst system having at least one catalytically active component, wherein the catalytically active component comprises at least one metal, wherein first a spherical activated carbon used as a catalyst carrier is subjected to an oxidation. Subsequently, the catalytically active component is applied, optionally followed by a reduction of the catalyst system obtained in said manner.

14 Claims, 2 Drawing Sheets

(51) Int. Cl.
  *C07C 57/30* (2006.01)
  *B01D 39/20* (2006.01)
  *B01J 37/16* (2006.01)
  *B01J 35/10* (2006.01)
  *B01J 23/16* (2006.01)
  *B01J 23/48* (2006.01)
  *B01J 23/70* (2006.01)
  *B01J 35/02* (2006.01)
  *A62D 9/00* (2006.01)
  *C01B 32/354* (2017.01)

(56) References Cited

U.S. PATENT DOCUMENTS

| | | |
|---|---|---|
| 2012/0208103 A1 | 8/2012 | Chang et al. |
| 2013/0184499 A1 | 7/2013 | Tanielyan et al. |

FOREIGN PATENT DOCUMENTS

| | | |
|---|---|---|
| JP | 2008183558 | 8/2008 |
| WO | 0183368 | 11/2001 |
| WO | 2013044080 | 3/2013 |
| WO | 2013068060 | 5/2013 |

* cited by examiner

CATALYST SYSTEM BASED ON SPHERICAL ACTIVATED CARBON AS A CARRIER AND USE THEREOF

CROSS-REFERENCES TO RELATED APPLICATIONS

This application is a National Stage filing of International Application PCT/EP 2014/003138, filed Nov. 25, 2014, claiming priority to DE 10 2013 020 233.7 filed Dec. 9, 2013, and to DE 10 2014 103 351.5 filed Mar. 12, 2014, entitled "CATALYST SYSTEM BASED ON SPHERICAL ACTIVATED CARBON AS A CARRIER AND USE THEREOF". The subject application claims priority to PCT/EP 2014/003138, DE 10 2013 020 233.7 and DE 10 2014 103 351.5 and incorporates all by reference herein, in their entirety.

BACKGROUND OF THE INVENTION

The present invention relates to the technical field of catalytically active systems and/or to the technical field of catalysts/catalytically active components on carrier materials.

The present invention more particularly relates to a method of preparing a catalyst system comprising at least one catalytically active component, in particular to a method of preparing a supported catalyst.

The present invention further relates to a catalyst system obtainable on the basis of the method according to the present invention and/or to a catalyst system as such, said catalyst system comprising at least one catalytically active component on a catalyst carrier, in particular at least one catalytically active component fixed to a catalyst carrier.

The present invention further also relates to methods of using the catalyst system of the present invention in the manufacture of filters and filter materials. The present invention further relates to methods of using the catalyst system of the present invention as a sorption store for gases or liquids or as a catalyst/catalyst carrier and also the use thereof for chemical catalysis. The present invention further relates to methods of using the catalyst system of the present invention in the catalysis of chemical processes and reactions. The present invention further relates to methods of using the catalyst system of the present invention in or as gas sensors or in fuel cells and also for sorptive, specifically chemisorptive, applications. The present invention further also relates to methods of using the catalyst system of the present invention for gas cleaning/purification and also for the removal of noxiants. The present invention further relates to methods of using the catalyst system to provide/reprocess cleanroom atmospheres. The present invention further also relates to protective materials as such, said protective materials being obtained by using the catalyst system of the present invention and/or comprising the catalyst system of the present invention. The present invention further also relates to filters and filter materials obtained by using the catalyst system of the present invention and/or comprising the catalyst system of the present invention.

A catalyst is generally a material/substance capable of raising the rate of a chemical reaction by lowering the activation energy without itself being consumed in the reaction.

Catalysts have immense technical and commercial significance in the prior art, for example in important catalytic processes, such as the so-called contact process for production of sulfuric acid, the catalytic process for methanol production and also the so-called Haber-Bosch process for industrial production of ammonia, and also the so-called Ostwald process for large scale industrial production of nitric acid by oxidation of ammonia. Catalysts are further employed in the synthesis of fine/specialty chemicals, in the synthesis of natural products and also in the manufacture of active pharmaceutical ingredients. More particularly, catalysts are also employed in catalytic hydrogenations.

The need for specific and powerful catalysts for use in chemical catalysis is generally high in the prior art, in particular because precise employment of catalysts enables faster and/or more energy-efficient chemical reactions. Hence the use of catalysts in chemical reactions is of immense commercial significance for that reason as well: a catalytic stage is believed to play a part in the underlying production/supply chain of about 80% of all chemical articles of manufacture.

In addition, catalysts also play an outstanding part in the area of environmental protection, in particular with regard to an exhaust gas aftertreatment in industry, for example in the context of industrial electricity generation and also in the treatment of exhaust gases in the field of road (passenger) transport.

Catalysts are in principle employable in the form of homogeneous or heterogeneous catalysts meaning that in the case of homogeneous catalysts, i.e., catalysts employed in homogeneous catalysis, the reactants underlying the reaction to be catalyzed and the catalyst are present in the same phase, whereas in the case of heterogeneous catalysts, i.e., catalysts employed in heterogeneous catalysis, corresponding reactants on the one hand and the catalyst on the other are present in different phases, for example as a solid catalyst and as liquid or gaseous reactants.

The advantages associated with employing heterogeneous catalysts reside in principle in particular in an occasionally improved separation/isolation of the catalyst from the reaction mixture, entailing the in-principle possibility of recycling the employed catalyst and/or of working up deactivated/inactive catalysts. Especially industrial processes often have a heterogeneous catalyst present in the form of a solid material and/or as a so-called contact (catalyst), while the reactants are employed in the form of gases or liquids. The aforementioned industrially established processes for example are such processes where the catalyst is employed in the form of a solid material.

Heterogeneous catalysts and/or catalysts in solid form often utilize metals and/or metal-containing compounds, such as metal salts and/or metal oxides, as catalysts. Catalysts of this type are for example employable therein in substance or alternatively in a form where the catalyst and/or its underlying catalytically active component is present on a carrier system and/or bound/fixed thereto.

Catalyst systems of this type, where the catalytically active component is present on a carrier, are generally known as supported catalysts.

Employing supported catalysts generally has the in-principle advantage of making it possible to realize larger surface areas and/or contact areas with the reactants to be converted, which generally leads to increased effectiveness and/or the employment of reduced amounts of catalyst with an attendant cost advantage.

Moreover, the employment of supported systems and/or catalysts is in principle associated with the advantage that the underlying catalysts are better to remove/separate from the reaction medium and also, in general, better to recycle. Especially catalysts employed in substance are difficult and/or very lossfull (in terms of catalyst mass) to segregate after reaction/conversion of the reactants, which generally serves to depress the economics and makes recycling of the catalysts used difficult in principle.

Supported catalysts/catalyst systems in the prior art may in principle take the form of supported structures that are compact or alternatively porous. The employment of so-called compact catalysts is associated in particular with the disadvantage that an efficient enlargement of surface area cannot be realized and therefore that catalytic activity can only be provided at the relatively small geometric surface area. By contrast, porous solids employed as catalyst carriers have enlarged surface areas which, as noted above, entails an increased effectiveness and/or a higher catalytic activity for a lower loading of catalyst.

Catalyst carriers employed include, for example, crystalline porous solids from the family of the zeolites, in particular in the field of petrochemistry and/or refinery technology to process/refine petroleum/crude oil. Pore sizes/diameters of zeolites are generally uniform, which provides a certain selective degree of reaction control through size alignment with the substances to be reacted. It is further in principle known in the prior art to employ silica, molecular sieves, metal oxides, such as aluminas, or alternatively ceramics as well as activated carbons as carrier systems for catalysts.

Carrier systems of this type are in principle also employed in order to enable a durable and/or elution-resistant fixing of specifically cost-intensive catalysts to reduce the respective losses during use and/or enable a corresponding recyclability, as noted above, and/or recovery of the catalyst system overall.

As far as the employment of activated carbon as a carrier material for catalysts specifically to obtain so-called activated carbon supported catalysts, in particular activated carbon supported noble metal catalysts, is concerned, the prior art generally employs activated carbons in the form of finely divided and/or pulverulent activated carbon (powdered carbon) and/or in the form of a finely ground powder, the corresponding particle sizes being in the lower µm range. Finely divided activated carbon is generally employed as a carrier system as an attempt to reduce limitations in the underlying mass transfer involved in the corresponding catalyzed target reaction, in particular through shortened diffusion/penetration paths into the porous structure of the activated carbon based carrier material. However, the employment of finely divided and/or pulverulent activated carbon as a catalyst carrier in the form of comparatively small particle sizes is associated with the central disadvantage that overall it is impossible to achieve optimum performance characteristics. For instance, the employment of finely divided activated carbon specifically in batch applications is caused by the low porosity in the filter cake bed and/or the high density of the bed formed from the underlying material to lead to inferior properties with regard to the segregation/separation of the catalyst/catalyst system after its use, in which connection it must be emphasized that the step of separating/filtering off the catalyst/catalyst system is an obligatory and/or absolutely required element of any catalytic batch process.

In-service conditions particularly of continuous catalytic processes employing pulverulent/finely divided activated carbon and/or powdered carbon in the reaction space are observed to result in an occasionally excessive densification of the catalyst system and hence in a high level of pressure drop and hence a reduced rate at which the reaction mixture comprising the corresponding reactants flows over the catalyst system. An excessive densification can also result when, as is often the case, the catalysts employed and/or the corresponding carrier materials lack abrasion hardness, and entails undesirable changes in the flow rate.

The performance characteristics of activated carbon supported catalyst systems are often also less than optimal in that the finely divided catalyst system is prone, particularly in a liquid medium comprising the reactants, to sludging and/or excessive densification, entailing a risk of plugging the reaction apparatuses and/or of excessively reducing the flow/filtration rate, adversely affecting catalytic conversion overall. Excessive densification of the catalyst system here may to a certain extent also result in "dead spaces" in the underlying apparatus, which result in a significantly reduced conversion of the reactants, which is similarly disadvantageous.

In general, the formation of sludged regions in the catalyst system is problematic/relevant in batch use in particular. Continuous catalytic applications where the underlying catalyst systems are for example introduced into corresponding reaction spaces, for example based on cartridge systems, and where a specifically continuous flow therethrough of a medium comprising the reactants takes place similarly give rise to the abovementioned high pressure drops with the corresponding lower flow rates for the catalyst system with the attendant disadvantages. Furthermore, to prevent the catalyst being dragged/flushed out by the continuous flow through the reaction system, there is often a need for costly filtration/retention devices which are prone to plugging.

It must accordingly be noted in summary that catalyst systems based on powderily/finely divided activated carbon as carrier material altogether do not always have adequate/satisfactory properties in respect of their application.

In order to reduce the disadvantages entailed by a small particle size, prior artisans have attempted to employ catalyst carriers based on particulate activated carbon while in principle contemplating in this regard starting materials for the activated carbon which are based on coconut shells, charcoal, wood (e.g., wood waste, peat, bituminous coal or the like). The activated carbons of the aforementioned type which result and/or are employed as catalyst carriers and may generally be in splint and/or granular form do in principle lead to a certain improvement in the performance characteristics, particularly with regard to the separation time in batch application, because this can be reduced on the basis of activated carbons, yet such activated carbons employed as catalyst carriers often have an insufficient level of mechanical stability, entailing an excessive attrition of the carrier material under in-service conditions, for example due to occasionally intensive agitation during the catalytic conversion. The low level of abrasion resistance on the part of such activated carbons then in turn leads via the corresponding comminution/grinding processes to finely divided particles entailing a high loss of catalytically active substance and the aforementioned disadvantages with regard to system sludgification/densification or the like.

In addition, the prior art concepts known for providing catalyst systems based on activated carbon as a carrier material are also disadvantageous because they often fail to enable optimal loading/fixing of the catalyst on the carrier material resulting not only in low amounts of catalyst being applied to the carrier but also in the frequent observation under in-service conditions of some release/leaching (elution) of the catalyst out of the carrier material, the leached amounts of catalyst being lost as a result, which is disadvantageous for technical as well as cost reasons. More particularly, the activated carbons which are employed in the prior art, in particular those which are based on coconut shells, often display a but low level of affinity for the catalyst to be applied/fixed and this—without wishing to be tied to this theory—is also caused by the underlying activated carbons often being hydrophobic at their pore surface and/or often not having an adequate amount of specifically polar functional groups to bind the catalyst (as is the case particularly with polymer based activated carbons, in particular PBSACs). However, this is detrimental to the loading properties as a whole, including specifically with regard to any durable fixing of the catalyst on the carrier system. The high loss of catalyst in relation to the underlying catalyst system similarly entails a reduction in the reactant conversion of the underlying catalytic reactions, which also serves to depress the economics of the catalyst systems employed.

Since conventional activated carbon is apolar and/or hydrophobic at its surface and therefore does not display any significant affinity for catalytically active components/catalysts to be applied/fixed which are employed for reactive/catalytic endowment of the activated carbon, the preparation/endowment of the activated carbon with the catalyst requires the employment of a large excess of catalyst substance in order to ensure any loading of the activated carbon at all. More particularly, the catalysts generally only adhere via purely physical interactions and may therefore also be removed again in part at least particularly on contact with liquids (e.g., as in elution processes or the like).

DE 29 36 362 C2 describes a method of preparing a palladium-carbon catalyst wherein reduction is used to deposit palladium on a carbon catalyst carrier suspended in an organic solvent. Palladium is stated in this context to be deposited as metal on the suspended carrier. The carbon carrier used is pulverulent activated carbon, carbon black or graphite. However, the catalysts described do occasionally entail the disadvantages described above, particularly regarding the segregation/recovery of the catalyst particularly in batch type catalytic processes as well as its performance characteristics in continuous catalytic processes, particularly with regard to pressure drop and/or flow rate.

It must thus be stated in summary that the prior art catalyst systems based on conventional activated carbons and/or pulverulent activated carbons as employed carrier material have both manufacturing—but also use-specific disadvantages, in particular with regard to the loading with a catalytically active component and also its fixing on the material on the one hand but also with regard to the use of the underlying systems in continuous and also batch type applications in catalysis.

BRIEF SUMMARY OF THE INVENTION

Against this background, the present invention therefore has for its object to provide catalyst systems and/or supported catalysts comprising at least one catalytically active component and also a corresponding method of manufacture wherein the prior art disadvantages described above shall be at least substantially avoided or alternatively at least ameliorated.

More particularly, a supported catalyst/catalyst system to be provided in the context of the present invention as having at least one catalytically active component shall have not only manufacturing—but also performance-specific advantages.

More particularly, such a catalyst system provided by the present invention as having at least one catalytically active component shall enable a high/efficient level of loading with the catalyst component while at the same time ensuring a durable and stable loading/endowment with the catalyst component.

The invention in this connection additionally seeks to provide a catalyst system which with regard to its application, in particular with regard to its preferred application in chemical catalysis, preferably on an industrial scale, not only batchwise but also continuous catalytic applications, has improved properties particularly in respect of the segregation/recovery/recycling (in batchwise processes in particular) and improved properties in the direction of a low/controllable pressure drop and high/controllable flow rates (in continuous catalytic processes in particular), while at the same time also providing optimized processing times and/or an enhanced catalytic activity overall.

More particularly, the present invention seeks to provide such a catalyst system which combines its high catalytic activity with outstanding mechanical properties, in particular with regard to the abrasion resistance and/or the bursting pressure of the underlying corpuscle-shaped structures. Similarly, the systems provided by the invention shall also be individually engineerable and/or custom tailorable in relation to the particular application/service scenario.

The present invention shall moreover provide an efficient method whereby the present catalyst system comprising at least one catalytically active component is obtainable.

As the applicant companies have now found, very surprisingly, the above-defined problem addressed by the present invention is unexpectedly solved when the catalyst carrier employed in the context of the present invention is purpose-directedly a spherical activated carbon which, prior to loading with a catalytically active component to provide the supported catalyst/catalyst system of the present invention, is purpose-directedly subjected to an oxidation, in particular a surface oxidation (i.e., an oxidation particularly of the internal surface area of the catalyst carrier), and wherein the activated carbon thus oxidized, specifically at its inner surface, is subsequently endowed with the catalytically active component, while the present invention also provides for the catalyst system thus obtained to be subsequently, i.e., after endowment with the catalytically active component, subjected to a reduction and/or reductive treatment.

In other words, the invention accordingly provides a specific catalyst system and/or a supported catalyst comprising at least one catalytically active component on a catalyst carrier, wherein the catalyst carrier is in the form of spherical activated carbon and wherein the catalytically active component is applied to the activated carbon while the activated carbon is in an oxidized form.

The catalyst system provided in the present invention is suitable, as will be elaborated hereinbelow, not only for use in the field of chemical catalysis, in particular on a (large) industrial scale, but also for corresponding filtering applications to remove, for example, noxiant and poisonous materials from a medium containing same. More particularly, the catalyst systems provided according to the present invention are also suitable for application in the context of protective materials, in particular for the civilian or military sector, in particular protective materials for NBC deployment.

DETAILED DESCRIPTION OF THE INVENTION

Figure 1:
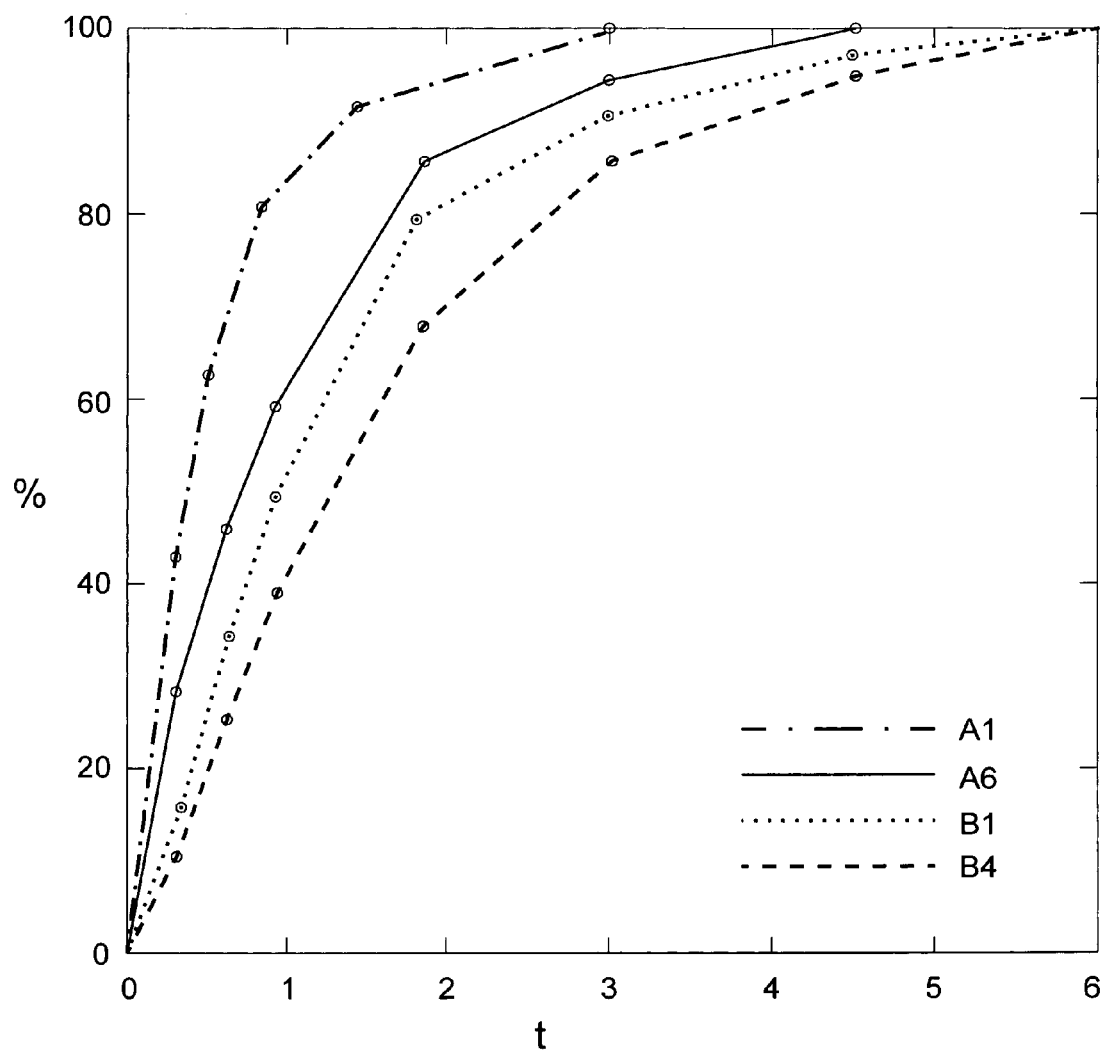
FIG. 1 provides the time course of the formation of hydrocinnamic acid from cinnamic acid using inventive and reference catalysts, and FIG. 2 provides the time course of the formation of hexanol from hexanal using inventive and reference catalysts.

To solve the problem defined above, the present invention accordingly proposes—in accordance with a first aspect of the present invention—the methods of preparing the catalyst system of the present invention, which comprises at least one catalytically active component, which are claimed in independent method claims. Further, specifically advantageous versions of the methods according to the present invention form the subject matter of respective dependent method claims.

The present invention further provides—in accordance with a second aspect of the present invention—the catalyst system of the present invention and/or the supported catalyst of the present invention, wherein said catalyst/catalyst system includes at least one catalytically active component and wherein the catalyst carrier employed is a spherical activated carbon which is in oxidized form when the catalytically active component is applied to it, in accordance with the independent claims relating to the catalyst system of the present invention. Further, specifically advantageous versions of the catalyst system according to the invention form the subject-matter of respective dependent claims.

The present invention still further provides—in accordance with a third aspect of the present invention—the uses according to the invention which are recited in the respective independent use claim.

The present invention yet still further provides—in accordance with a fourth aspect of the present invention—the protective materials of the present invention, in particular for the civilian or military sector, in particular protective apparel, as per the respective independent claim.

The present invention yet still further provides—in accordance with a fifth aspect of the present invention—filters and filter materials, in particular for removal of noxiant, odorant and poisonous materials of any kind, as per the respective independent claim. Further, specifically advantageous versions of the filters and filter materials according to the present invention form the subject matter of respective dependent claims.

It will be readily understood that, in the hereinbelow following description of the present invention, such versions, embodiments, advantages, examples or the like, as recited hereinbelow in respect of one aspect of the present invention only, for the avoidance of unnecessary repetition, self-evidently also apply mutatis mutandis to the other aspects of the present invention without the need for an express mention.

It will further be readily understood that any values, numbers and ranges recited hereinbelow shall not be construed as limiting the respective value, number and range recitations; a person skilled in the art will appreciate that in a particular case or for a particular use, departures from the recited ranges and particulars are possible without leaving the realm of the present invention.

In addition, any hereinbelow recited value/parameter particulars or the like can in principle be determined/quantified using standardized or explicitly recited methods of determination or else using methods of determination/measurement which are per se familiar to a person skilled in the art.

As for the rest, any hereinbelow recited relative/percentage, specifically weight-based, recitations of quantity must be understood as having to be selected/combined by a person skilled in the art within the context of the present invention such that the sum total—including where applicable further components/ingredients, in particular as defined hereinbelow—must always add up to 100% or 100 wt %. But this is self-evident to a person skilled in the art.

Having made that clear, the present invention will now be more particularly described.

In a first aspect of the present invention, the present invention relates to a method of preparing a catalyst system comprising at least one catalytically active component, in particular a supported catalyst, wherein the catalytically active component comprises and/or consists of at least one metal, wherein first a spherical activated carbon employed as catalyst carrier is subjected to an oxidation, in particular a surface oxidation, and wherein thereafter the activated carbon thus oxidized, specifically at its surface, is endowed and/or loaded and/or coated and/or impregnated with the catalytically active component, in particular by applying and/or contacting, preferably fixing, the catalytically active component to the catalyst carrier, optionally followed by a reduction (i.e., either as a surface reduction specifically of the previously oxidized activated carbon and/or alternatively as a reduction of the catalytically active component, in particular of the metal/metal compound underlying the catalytically active component, preferably for purposes of catalyst activation) of the catalyst system thus obtained.

As mentioned, a fundamental concept of the present invention thus consists in employing a very specific activated carbon as a carrier material for accommodation/endowment with a catalytically active component, wherein the activated carbon employed according to the present invention is firstly employed in spherical form and secondly is subjected in a precise manner to an oxidative treatment and/or a surface oxidation before endowment with the catalytically active component.

The precise deployment of a spherical form of activated carbon, i.e., activated carbon having a very specific and/or defined shape, surprisingly also leads to a significant improvement in the performance characteristics of the activated carbon provided according to the present invention not only in respect of the deployment of the catalyst system provided according to the present invention in batchwise catalytic applications but also in respect of the deployment of the catalyst system provided according to the present invention in continuous catalytic applications. This is because the specific shape on the basis of discrete spheres provides an improved bed porosity for batchwise applications, which not only prevents sludge formation in the reaction system but also improves the segregation/recovery of the catalyst from the reaction system significantly. On the other hand, the improved bed properties of the catalyst system according to the present invention lead to lower pressure drops while at the same time the accessibility of the catalyst system to reactant/starting materials to be converted is high, so the catalyst system of the present invention makes possible even high flow rates therethrough for a medium comprising the reactant/starting materials to be converted.

As more fully elaborated hereinbelow, a precise adjustment in the particle sizes/diameters of the underlying spherical activated carbon provides altogether custom-tailored catalytic systems having respectively optimized performance characteristics, particularly with regard to the recovery of the catalyst system and/or the flow behavior and/or the pressure drop, while at the same time the catalytic activity of the catalyst system according to the invention is further improved. More particularly, pressure drop and/or flow rate can be controlled and/or adjusted by predetermining the particle size, making it possible to provide optimized systems even against the particular service and/or application background.

Thus it is a spherical form of activated carbon, i.e., a spherocarbon, which is employed in the present invention. Spherical activated carbon has a number of further advantages over other forms of activated carbon, such as powdered activated carbon, splint carbon, granulocarbon and formed carbon or the like: spherical activated carbon is to a high degree free-flowing, abrasion resistant and/or dustless, and hard.

Extremely abrasion-resistant and/or mechanically stable spherical activated carbons of the type provided in particular by the hereinbelow further defined specific activated carbons based on organic polymers, in particular on sulfonated organic polymers, are purposely employed in the present invention for the catalyst carrier employed. And in this connection it is utterly surprising in the context of the present invention that any sulfur present in the activated carbon, wherein the sulfur content may be for example up to 0.1 wt %, based on the activated carbon, is not detrimental to the catalytic function of the catalyst system according to the present invention and/or does not lead to any disadvantageous impairment of the catalytic activity and particularly not to any so-called catalyst poisoning.

The high level of abrasion resistance and/or mechanical stability ensures in particular that the catalyst system employed according to the present invention does not wear even under exposure to and/or agency of flowing and/or shearing forces, stirring forces or the like, resulting in at least essentially no significant attrition in the course of service. The invention thus provides a very durable and mechanically resistant catalyst system, leading to minimized losses of material and minimal losses of catalytic activity and also, in general, to simplified handling for the catalyst system of the present invention.

Moreover, the oxidation, specifically surface oxidation (i.e., oxidation specifically of the inner surface), of the activated carbon employed before the step of endowing the catalytically active component has surprisingly succeeded, in the context of the present invention, in ensuring a high and simultaneously durable/stable loading with the catalytically active component of the activated carbon employed as carrier material, leading to a distinctly enhanced catalytic activity coupled with simultaneously improved stability for the catalyst system of the present invention, in particular since leaching/detachment of the catalytically active component out of the carrier material is reduced and/or avoided in the application scenario. Without wishing to be tied to this theory, the precise oxidation, i.e., surface oxidation, of the activated carbon is believed to lead to the formation of specific oxygen-containing functional groups on the activated carbon employed according to the present invention and/or in the pore system thereof, not only in the region of the micro-, meso- but also of the macropores, which enhances the affinity of the activated carbon for the catalytically active component employed according to the present invention. The oxidative or to be more precise surface-oxidative treatment of the activated carbon, which the present invention requires to be carried out before endowing with the catalytically active component, generates/provides a less hydrophobic and/or a hydrophilic surface on the activated carbon and/or specific functional groups on the surface of the activated carbon and/or in the pore system of the activated carbon, and this leads in an utterly surprising manner to a significant improvement in the incorporation of the catalytically active component.

It is similarly utterly surprising in this connection that the catalyst system of the present invention, which is based on a spherical activated carbon having a defined particle shape and/or size and subjected to an oxidation before loading with the catalytically active component, should have a significantly improved catalytic activity even compared with powdered activated carbons. It is utterly surprising in this connection that the catalyst system of the present invention does not suffer any significant restrictions/limitations as regards mass transfer, in particular in relation to the underlying reactants/starting materials, in the pore system of the activated carbon, this being attributable in particular also to the defined porous structure, as elaborated hereinbelow, of the activated carbons employed according to the present invention. It has emerged as particularly advantageous for the present invention for a micro- and mesoporous activated carbon, in particular a mesoporous activated carbon, to be employed as catalyst carrier for the catalyst system of the present invention.

More particularly, it is utterly surprising that the catalyst system provided according to the present invention should also have a high level of catalytic activity even at relatively large particle sizes as compared with powdered carbon in particular. What has been accomplished in this connection through the cooperation of the measures provided according to the present invention—without wishing to be tied to this theory—is enabling a particularly uniform and high loading of the activated carbon with the catalytically active component while at the same time reducing the mass transfer/diffusion limitations in the catalyst system that are detrimental to catalytic activity.

The concept of the present invention, in particular the specific alignment between the carrier system on the one hand and the catalytically active component on the other, prevents, at least essentially, any plugging of the pore system underlying the activated carbon by the catalytically active component, for example by an excessive crystal size in connection with crystallizing out of the metal salts, which still further improves the performance capability of the catalyst system provided according to the present invention.

The present inventors are thus the first to succeed in providing, on the basis of the method according to the present invention, a very specific catalyst system having a very specific activated carbon as carrier material and endowed with at least one catalytically active component in a precise manner, said catalyst system having significant advantages and improved properties as compared with prior art systems and therefore also be very useful in chemical catalysis and this not only in relation to batchwise but also in relation to continuous catalytic applications. The catalyst system provided by the method of the present invention has not only improved mechanical but also improved catalytic properties, entailing shorter processing times and a higher recovery rate coupled with reduced time requirements and outstanding recycling for the underlying catalyst and/or catalytically active component. In addition, as noted above, the catalyst system of the present invention displays improved flow properties coupled with minimal pressure problems specifically on employment/use in the form of (loose) beds.

The catalyst system of the present invention, which is provided on the basis of the method of the present invention, is further also suitable for use in and/or as filter and/or filter materials, in particular for disarming noxiants and/or poisonous materials or the like.

The catalyst system provided on the basis of the method according to the present invention thus combines outstanding mechanical properties on the one hand with outstanding catalytic properties on the other.

The method of the present invention is the basis for ultimately achieving an effective endowment of the activated carbon employed for the carrier material of at least one catalytically active component to obtain the catalyst system of the present invention. More particularly, the purpose-directed oxidation, specifically surface oxidation, of the activated carbon employed significantly improves the endowment with the catalytically active component not only with regard to the loading quantity but also with regard to the stability/durability of the catalytic endowment.

The term "catalyst system" as used in the present invention, interchangeably with supported catalyst, is to be understood in the context of the present invention as having a very broad meaning, referring in particular to a functional unit based on a catalytically active component on the one hand and on a carrier material on the other, although the underlying catalytic properties are determinatively attributable to the catalytically active component, which to this end comprises and/or consists of at least one metal. The invention provides in this context that the spherical activated carbon employed is provided the catalytically active component, in particular in the form of an endowment/loading/coating/impregnation, in particular on the basis of fixing the catalytically active component on the underlying catalyst carrier, to obtain the catalyst system of the present invention.

Furthermore, the terms "endowment" and/or "loading" and/or "coating" and/or "impregnation" as used for the purposes of the present invention relate in particular to such an endowment of the activated carbon employed in the invention as carrier material with the catalytically active component whereby the outer and/or inner surface structure of the activated carbon employed inclusive of the respective pores, in particular micro-, meso- and/or macropores, are at least partly and/or portionally in contact and/or endowed with and/or provided the catalytically active component. This catalytically active component is believed to develop—without wishing to be tied to this theory—on the activated carbon surface a kind of catalytic structure and/or chemisorptive properties capable of complementing the physisorptive properties of the activated carbon, so the catalyst system provided on the basis of the method according to the invention combines in principle not only chemisorptive but also physisorptive properties in one and the same material. And the catalytically active component is present in and/or on the activated carbon in particulate and/or crystal-shaped form in particular.

The term "spherical", interchangeable with "ball shaped", as used herein for the activated carbon employed in the present invention as carrier material is to be understood as having a very broad meaning, and as relating particularly to an at least essentially ideal spherical/ball-shaped form of activated carbon, but also to such shapes and/or physical inclinations of the activated carbon employed which differ from the sphere or ball shape, such as a configuration of the activated carbon in the form of a (rotational) ellipsoid or the like. The term "spherical" further also comprehends such spherical and/or ellipsoidal forms of activated carbon wherein the activated carbon may display bulges and/or indents, bends, divots, cracks or the like. The invention is thus determinatively geared to employing a spherical form of activated carbon and/or a spherical carbon and/or a ball-shaped activated carbon.

The present invention in accordance with this aspect of the invention similarly also relates to a method, particularly as defined above, of preparing a catalyst system comprising at least one catalytically active component, in particular a supported catalyst, wherein at least one catalytically active component is fixed on a catalyst carrier, wherein the catalytically active component comprises and/or consists of at least one metal, wherein said method comprises the following steps in the hereinbelow specified sequence (a) to (d):

(a) preparing and/or providing a spherical activated carbon employed as catalyst carrier;

(b) oxidizing, in particular surface oxidizing, the spherical activated carbon;

(c) endowing and/or loading and/or coating and/or impregnating the oxidized, in particular surface oxidized, activated carbon with the catalytically active component particularly to obtain the catalyst system, in particular by applying and/or contacting, preferably fixing, the catalytically active component to the catalyst carrier, and (d) optionally reducing the catalyst system obtained in step (c), in particular the activated carbon endowed with the catalytically active component.

From this aspect, the present invention more particularly also relates to a specifically as above-defined method of preparing a catalyst system comprising at least one catalytically active component, in particular a supported catalyst, wherein at least one catalytically active component is applied and/or fixed to a catalyst carrier, wherein first a spherical activated carbon employed as catalyst carrier is subjected to an oxidation, in particular to a surface oxidation, wherein the activated carbon thus obtained, which is preferably in the form of a multiplicity of spherical particles of activated carbon, is contacted, in particular wetted and/or loaded and/or covered, with an optionally dissolved and/or dispersed catalytically active component. In particular, in this context subsequently any solvent and/or dispersant medium used for dissolving and or dispersing any catalytically active component in excess and/or not taken up by the activated carbon can be removed and/or separated off.

In other words, the present invention thus provides in particular that, before loading and/or endowment with the catalytically active component, the activated carbon employed in accordance with the invention be oxidized and/or subjected to an oxidative treatment, in particular in order thereby to enhance its affinity for the catalytically active component, entailing an improved loading/endowment of the catalyst system according to the present invention with the catalytically active component, particularly with regard not only to the loading quantity but also with regard to the durability and/or (elution) stability of the loading.

As far as the method of the present invention is further concerned, it is advantageous for the purposes of the present invention when the activated carbon provided/prepared in step (a) specifically is obtained by carbonizing and subsequently activating a starting material based on organic polymers, followed by an oxidation or oxidative treatment, in step (b) specifically, wherein the oxidation or oxidative treatment is carried out before the step of applying, in particular fixing, the catalytically active component provided in step (c) in particular.

Optionally this may be followed by a reduction or reductive treatment, in particular in the step (d), wherein the reduction or reductive treatment may be carried out after the step of applying, in particular fixing, the catalytically active component, in particular after and/or following step (c).

The present inventors have found a particular advantage in performing the invention by employing an activated carbon based on a very specific starting material.

Therefore, in a particularly preferred embodiment of the present invention, the activated carbon provided/prepared specifically in step (a) is obtained from a starting material based on organic polymers, in particular on sulfonated organic polymers, preferably based on divinylbenzene-crosslinked polystyrene, preferably based on styrene-divinylbenzene copolymers, in particular by carbonizing and then activating the starting material.

This is because an activated carbon obtained on the basis of the starting materials as used above has, firstly, a high mechanical abrasion resistance and/or a high bursting pressure, secondly a defined shape in a spherical configuration of the activated carbon and thirdly also a defined porosity and/or pore structure, in that the adduced parameters in particular the porosity, of the activated carbon are also in a way custom-tailorable via the manufacturing conditions chosen, particularly also with regard to the pore distribution in terms of micro-, meso- and macropores.

The activated carbon based on organic polymers, as defined above, which is employed with particular preference for the purposes of the present invention is very particularly free-flowing, abrasion-resistant and also dustless and hard, which leads to a significant improvement in the corresponding properties of the catalyst system according to the present invention. An activated carbon of this type moreover ensures good loading with the catalytically active component and enables in service an optimal form of penetration into the pore system by the reactant/starting materials to be converted.

As far as the activated carbon employed with particular preference for the purposes of the present invention, obtained by carbonizing and then activating a starting material based on organic polymers, is concerned, the invention may provide that the divinylbenzene content of the starting material is in the range from 1 wt % to 20 wt %, in particular 1 wt % to 15 wt %, preferably 1.5 wt % to 12.5 wt %, preferably 2 wt % to 10 wt %, based on the starting material.

In this connection, the starting material may be of the gel type or of the macroporous type, in particular of the gel type.

The invention may provide in particular that the catalyst carrier employed is a polymer-based spherical activated carbon (PBSAC) and/or that the activated carbon is a polymer-based spherical activated carbon (PBSAC).

The activated carbon employed is in principle obtainable by known methods of the prior art. They more particularly comprise spherical sulfonated organic polymers, in particular on the basis of dinvylbenzene-crosslinked polystyrene, being for this purpose carbonized and then activated to form the particular activated carbon, in particular as noted above. Further details in this regard may be revealed for example in the printed publications DE 43 28 219 A1, DE 43 04 026 A1, DE 196 00 237 A1 and also EP 1 918 022 A1 and/or in the same patent family's co-member equivalent U.S. Pat. No. 7,737,038 B2, the respective content of which is hereby fully incorporated therein by reference. Activated carbons employed for the purposes of the present invention are generally commercially available. It is more particularly possible to employ activated carbons as marketed for example by Blücher GmbH, Erkrath, Germany, or by AdsorTech GmbH, Premnitz, Germany.

According to the present invention, the activated carbon may have a fractal dimension of open porosity in the range from 2.6 to 2.99, especially 2.7 to 2.95, and preferably 2.8 to 2.95. More particularly, the activated carbon may have a fractal dimension of open porosity of at least 2.7, in particular at least 2.8, preferably at least 2.85, more preferably at least 2.9. The fractal dimension of open porosity is a measure of the micro roughness of the inner surface of the activated carbon. Further details in this regard including particularly for determining the fractal dimension of activated carbons employed for the purposes of the present invention may be viewed in the printed publications DE 102 54 241 A1, WO 2004/046033 A1, EP 1 562 855 B1 and also the same patent family's co-member equivalent US 2006/148645 A1, in particular in Example 4 of the respective printed publications. The respective content of the produced printed publications is hereby fully incorporated by reference. The aforementioned fractal dimensions lead to further improved catalytic properties on the part of the catalyst system obtained using the method of the present invention.

The oxidizing agent employed in connection with the oxidation carried out in step (b) in particular may generally for the purposes of the present invention utilize a multiplicity of reagents/compounds. In principle, the oxidation process as described hereinbelow is carried out for a defined period with or without heating and/or temperature manipulation.

Regarding specifically the activated carbon oxidation carried out in step (b) in particular, the invention here provides that the oxidation, specifically surface oxidation of the activated carbon be carried out by using at least one oxidizing agent. In this context, the oxidizing agent should be selected from the group of oxygen, ozone, organic or inorganic oxides and peroxides and also organic or inorganic acids and peracids and combinations thereof, preferably from the group of oxygen, hydrogen peroxide ($H_2O_2$), nitric acid ($HNO_3$), nitrogen oxides (preferably NO and/or $NO_2$) and sulfuric acid ($H_2SO_4$) and also combinations thereof.

The term "surface oxidation" as used for the purposes of the present invention is to be understood as meaning in particular an oxidation of surfaces of the activated carbon employed as starting material which are in contact with the environment containing in particular the oxidizing agent and/or which are capable of being accessed from the outside by the oxidizing agent employed for the purposes of the present invention. What is concerned here in particular also includes the pore system of the activated carbon in the form of macro-, meso- and micropores.

Without wishing to be limited and/or tied to this theory, the methodology of the present invention, involving as it does the practice of a (surface) oxidization is believed to produce an oxidized layer particularly on the (pore) surface of the activated carbon, which generally has oxygen-containing functional groups as described hereinbelow. The endowment with the catalytically active component after the surface oxidation then takes place—again without wishing to be limited and/or tied to this theory—particularly in the region of the oxidized (boundary) layer, while the oxygen-containing functional groups enhance the affinity for and particularly also the interaction with the catalytically active component and/or function so to speak as binding and/or anchoring sites for the catalytically active component employed according to the present invention.

The endowment of the active carbon with the catalytically active component after the oxidation in the context of the method according to the invention thus provides the catalyst system of the present invention as such, comprising catalytic and/or reactive surfaces.

According to the present invention, the oxidation, specifically surface oxidation, of the activated carbon in step (b) in particular may be effected by heating, in which connection the surface oxidation may be effected at such temperatures as to effect a reaction of the oxidizing agent with the activated carbon to form oxygen-containing functional groups at the surface of the activated carbon. For example, the oxidation, specifically surface oxidation, of the activated carbon may be carried out in the temperature range from −20° C. to 1000° C., in particular 0° C. to 700° C., preferably 10° C. to 600° C., more preferably 20° C. to 500° C., yet more preferably 250° C. to 500° C. Therefore oxidation, in particular surface oxidation, of the activated carbon may be carried out for a period of up to 48 h, in particular up to 24 h, preferably up to 12 h. Furthermore oxidation, in particular surface oxidation, on the activated carbon is carried out for a period in the range from 1 minute to 600 minutes, in particular 5 minutes to 500 minutes, preferably 10 minutes to 400 minutes. The selection of the temperature and also of the periods underlying the oxidation may more particularly be made against the background of the oxidizing agent employed and/or the desired degree of oxidation.

In a particular embodiment of the present invention, the oxidation, in particular surface oxidation of the activated carbon in step (b) in particular is carried out by using at least one oxidizing agent, wherein the oxidizing agent is selected from the group of inorganic or organic oxides and peroxides and also inorganic or organic acids and peracids and combinations thereof, preferably from the group of hydrogen peroxide ($H_2O_2$), nitric acid ($HNO_3$), nitrogen oxides (such as NO and/or $NO_2$) and sulfuric acid ($H_2SO_4$). This surface oxidation should be carried out in the temperature range from −20° C. to 500° C., especially −15° C. to 400° C., preferably −10° C. to 350° C., more preferably −5° C. to 300° C., yet more preferably 0° C. to 250° C., most preferably 0° C. to 120° C.

In an alternative embodiment of the present invention, the oxidation, in particular surface oxidation, of the activated carbon is carried out by using at least one oxidizing agent, said oxidizing agent being selected from the group of oxygen and ozone, preferably oxygen. In this case, the surface oxidation should be carried out in the temperature range from 100° C. to 1000° C., particularly 150° C. to 900° C., preferably 200° C. to 750° C., more preferably 225° C. to 600° C., yet more preferably 250° C. to 500° C., most preferably 250° C. to 450° C.

Where, in the context of the invention, use is made in particular of oxygen, which can be sent particularly in the form of atmospheric air to the activated carbon to be oxidized, the oxidation is also referred to as a thermal oxidation, since it generally takes place under heating, whereas the oxidation can also be referred to as a chemical oxidation when the oxidizing agents used are in the form of hydrogen peroxide, nitric acid and/or sulfuric acid, since in this case no additional heating is required depending on the reagent used, although this additional heating may in general also be applied here. More particularly, the aforementioned oxidizing agents may be employed in gaseous and/or the liquid form, in particular in the form of preferably aqueous solutions and/or dispersions, as will in principle be known as such to a person skilled in the art.

In the particular embodiment of the present invention, the oxidation, in particular surface oxidation, of the activated carbon in step (b) in particular is carried out with the formation of a hydrophilic surface on the activated carbon. More particularly, the oxidation, in particular surface oxidation, of the activated carbon may be carried out with formation of oxygen-containing functional groups on the surface of the activated carbon. More particularly, the oxidation, in particular the surface oxidation, of the activated carbon may lead to a formation of oxygen-containing functional groups particularly on the surface of the activated carbon. In this context, the oxidizing functional groups may be selected from acidic and basic oxidizing functional groups and also their combinations, in particular acidic and basic surface oxides. More particularly, the oxygen-containing functional groups may be selected from hydroxyl, carboxyl, carbonyl, anhydride, lactone, quinone, pyrone, chromene and ether groups and also their combinations.

According to the present invention, the oxidation, in particular the surface oxidation, of the activated carbon may be carried out such that the resulting oxidized, specifically surface-oxidized, activated carbon has a content of oxygen-containing functional groups, charged and/or suppressed as content of volatile matter content ("VMC") and based on the dry weight of the oxidized activated carbon, at least 1 wt %, particularly at least 2 wt %, preferably at least 3 wt %, more preferably at least 4 wt %, and/or in the range from 1 wt % to 30 wt %, in particular 1.5 wt % to 25 wt %, preferably 2 wt % to 20 wt %, more preferably 3 wt % to 15 wt %. In this context, the content of oxygen-containing functional groups is adjustable via temperature and/or duration and/or type and/or concentration in terms of oxidizing agent.

In this context, the method of the present invention makes it possible to custom tailor the oxidation process particularly with regard to the subsequent endowment with the catalytically activated component.

Therefore, in the context of the method according to the present invention, the oxygen content of the surface-oxidized activated carbon is significantly enhanced as compared with the initial activated carbon employed, which generally has an oxygen content of less than 1 wt %, expressed as volatile matter content ("VMC") and based on the dry weight of the initial activated carbon. The reported oxygen content is based in particular on the oxidized activated carbon before being subjected to the optional reduction of the present invention.

The volatile matter content "VMC" functions in general as a measure of the degree of oxidation and relates in particular to the surface oxides formed by the oxidation. More particularly, the volatile matter content is quantifiable on the basis of ISO 562:1981. More particularly, the volatile matter content "VMC" is quantifiable on a previously dried surface-oxidized activated carbon in the course of corresponding heating for a period of 7 minutes to 900° C. under inert conditions.

The purpose-directed establishment of the level of oxygen-containing functional groups also makes it possible to predetermine/influence the amount of the catalytically active component employed thereafter in step (c) in particular. In this context, a person skilled in the art will always be able to select and mutually align the respective properties so as to achieve the desired loading with the catalytically active component within the meaning of the present invention.

The oxidative treatment of the activated carbon similarly changes/establishes the pH, specifically the surface pH, of the oxidized activated carbon:

The present invention may provide for instance that the oxidation, specifically surface oxidation, changes with the pH, specifically the surface pH, of the oxidized, specifically surface-oxidized, activated carbon by a value of at least 0.25, in particular at least 0.5, preferably at least 0.75, more preferably at least 1, yet more preferably at least 1.5, based on the non-oxidized (initial) activated carbon.

More particularly, the acidity of the oxidized, specifically surface-oxidized activated carbon may be increased and/or the pH, in particular surface pH, of the oxidized, specifically surface-oxidized activated carbon reduced, in particular by a value of at least 0.25, in particular at least 0.5, preferably at least 0.75, more preferably at least 1, yet more preferably at least 1.5. Furthermore, the basicity of the oxidized, specifically surface-oxidized, activated carbon may also be increased and/or the pH, specifically surface pH, of the oxidized, specifically surface-oxidized, activated carbon increased, particularly by a value of at least 0.25, particularly at least 0.5, preferably at least 0.75, more preferably at least 1, yet more preferably at least 1.5.

The pH values specified above relate particularly to the oxidized activated carbon in its state before any reduction of the activated carbon is carried out.

It may further be provided that the oxidation, specifically surface oxidation, carried out in step (b) in particular is followed and specifically the endowment/loading/coating/impregnating with the catalytically active component is preceded by a step of cleaning up and/or drying the oxidized activated carbon, in particular before step (c). The cleanup may for this purpose be effected using at least one washing operation in a liquid, in particular water. The drying in this connection may be carried out under reduced (air) pressure. More particularly, the drying may be effected at a (air) pressure in the range from 0.01 Pa to 100 Pa, in particular 0.1 Pa to 10 Pa.

The drying step may thus be carried out after step (b) and specifically before step (c).

The catalytically active component employed in step (c) in particular may as such, in the context of the present invention, include and/or consist of at least one metal, in particular in the form of a metal compound, preferably in the form of an ionic metal compound, and/or in particular in elemental form. This provides a particularly good catalytic activity.

The present invention may provide to this end in particular that the catalytically active component include at least one metal in a positive oxidation state/number, in particular at least one metal cation. The oxidation state/number of the metal may here reside in the range from +I to +VII, in particular in the range from +I to +IV, preferably in the range from +I to +III and more preferably be +I or +II. In relation to simple ions, the oxidation number corresponds to the charge number, whereas in the case of multinuclear ions, so-called clusters in particular, the oxidation number may differ from the charge number, as such will be well known to a person skilled in the art.

The present invention may provide more particularly that the catalytically active component include at least one metal having the oxidation state/number of zero. In this context, the metal is thus more particularly present in the elemental state and/or in elemental form. The metal concerned here may more particularly comprise a noble metal, preferably Au, Ag, Pd, Pt, Ir, Rh and/or Ru, preferably Au, Ag, Pd and/or Pt. The noble metal may in principle also be employed in the present invention in the form of a compound, in particular in the form of a salt, in which case the reduction which is carried out according to the present invention may particularly be used to effect a corresponding conversion into the elemental form and/or into the oxidation state of zero (catalyst activation).

In a preferred embodiment of the present invention, the catalytically active component may include at least one metal from the main or transition groups of the periodic table or at least one lanthanide. Similarly, the catalytically active component may include at least one metal selected from elements in main group IV or transition groups I, II, III, IV, V, VI, VII and VIII of the periodic table, particularly from elements in main group IV or transition groups I and II of the Periodic Table.

It is preferable here for the purposes of the present invention when the catalytically active component includes at least a metal selected from the group of Cu, Ag, Au, Zn, Hg, Sn, Ce, Ti, Zr, V, Nb, Cr, Mo, W, Mn, Fe, Bi, Ru, Os, Co, Rh, Re, Ir, Ni, Pd and Pt, especially Fe, Bi, V, Cu, Pb, Zn, Ag, Sn, Pd, Pt, Ru and Ni, preferably Fe, Bi, V, Cu, Pt, Ru and Pb, preferably Pd, Pt and Ru.

In general, the catalytically active component should include at least one metal compound which is preferably soluble and/or dispersible in a specifically aqueous and/or specifically aqueous-based solvent and/or dispersant medium, and which is preferably based on at least one above-defined metal.

The present invention may provide in particular that the catalytically active component include at least one organic or inorganic metal compound, preferably based on at least one above-defined metal, in particular a metal salt or a metal oxide, preferably a metal salt.

More particularly, the catalytically active component should include at least one organic or inorganic metal salt, preferably based on at least one above-defined metal, wherein the salt may be selected from the group of halogen salt, sulfates, sulfides, sulfites, nitrates, nitrites, phosphates, phosphides, phosphites, carbamates, alkoxides and carboxylic acid salts, in particular halide salts and carboxylic acid salts.

The present invention may provide in particular that the catalytically active component include at least one metal halide, preferably based on at least one above-defined metal, in particular a fluoride, chloride, bromide or iodide, preferably chloride, and/or at least one carboxylic acid salt of a metal, preferably based on at least one above-defined metal, in particular acetate.

The present invention may further provide that the catalytically active component include at least one metal compound selected from the group of palladium chloride, hexachloroplatinic acid, ruthenium chloride, copper chloride, iron chloride, vanadium chloride, and lead chloride, in particular palladium chloride, hexachloroplatinic acid, ruthenium chloride. Regarding the procedure envisaged by the invention in step (c) in particular, the invention is advantageous when the catalytically active component is employed in the form of a specifically aqueous and/or specifically aqueous-based solution/dispersion, in particular for purposes of endowing/loading/coating/impregnating the oxidized, in particular surface oxidized, activated carbon.

The invention thereby ensures that the step of endowing the carrier material based on the activated carbon employed is performable with the catalytically active component in the form of the corresponding solution/dispersion, leading to a particularly homogeneous endowment of the active carbon with the catalytically active component. Subsequently, i.e., after contacting the activated carbon with the corresponding solution/dispersion of the catalytically active component, the solvent/dispersant medium should be removed in particular.

The term "solution"/"dispersion" as used in this context of the present invention is more particularly to be understood as meaning that, in the underlying amounts/concentrations, the catalytically active component is in an at least essentially completely dissolved/dissociated/dispersed state in the underlying solvent/dispersant medium. It may be provided for example in the context of the present invention that for purposes of endowing/loading the activated carbon with the catalytically active component, the activated carbon employed according to the invention is immersed in/saturated with a corresponding solution/dispersion of the catalytically active component. The invention thereby ensures in particular that the underlying solution/dispersion will fill at least essentially the entire porous system in the activated carbon, leading to a homogeneous loading of the activated carbon with the catalytically active component.

Contacting the activated carbon with the solution/dispersion of the catalytically active component for purposes of endowing the activated carbon with the catalytically active component may equally and non-limitingly be effected by spraying, specifically sprayed impregnation, vacuum processes and/or vacuum pressure processes. The respective processes are as such well known to a person skilled in the art.

Therefore, in a particularly preferred embodiment of the present invention, the underlying activated carbon to be endowed with the catalytically active component is as such brought into contact with, in particular as defined above, with the solution/dispersion of the catalytically active component. The endowment/loading/coating/impregnation of the underlying activated carbon is achieved subsequently specifically by removing the solvent/dispersant medium employed, the catalytically active component then being present in/on the activated carbon in a particulate, preferably crystalline, form in particular.

The present invention may provide in this connection that the solution/dispersion should comprise water as solvent/dispersant medium. More particularly, the solution/dispersion may further contain at least one organic or inorganic acid or base, preferably hydrochloric acid, specifically to improve the solubility/dispersal of the catalytically active component employed. The employment of organic solvent/dispersant media may in principle also be contemplated.

In general, the catalytically active component should be present in the solution/dispersion in an at least essentially crystal- and/or crystallite-free form. More particularly, the catalytically active component should be present in the solution/dispersion in an at least essentially dissolved, in particular at least essentially dissociated, form. This likewise serves to improve the penetration behavior by the solution/dispersion into the activated carbon or to be more precise into the pore system of the activated carbon to be endowed with the catalytically active component.

In this context, it has been found to be advantageous for the catalytically active component to be present in the solution/dispersion in an at least essentially crystal- and/or crystallite-free form. In addition, the catalytically active component should be present in the solution/dispersion in an at least essentially dissolved, in particular at least essentially dissociated, form. This serves to further improve in particular the penetration behavior of the catalytically active component solution/dispersion used for the endowing step.

More particularly, the solution/dispersion should contain the catalytically active component in amounts ranging from 0.01 wt % to 80 wt %, in particular from 0.1 wt % to 60 wt %, preferably from 1 wt % to 50 wt %, more preferably from 2 wt % to 40 wt %, based on the solution and/or dispersion and reckoned as metal.

An embodiment of the present invention provides in step (c) in particular that the step of endowing and/or loading and/or coating and/or impregnating the oxidized, specifically surface oxidized, activated carbon with the catalytically active component comprises applying and/or contacting, preferably fixing, the catalytically active component to the oxidized, specifically surface oxidized, activated carbon.

The invention may provide in this context that the applying and/or contacting, preferably fixing, is effected by immersing and/or saturating in and/or wetting and/or covering and/or coating and/or spraying and/or spray dispensing the oxidized, specifically surface oxidized, activated carbon into and/or with the catalytically active component. In this context, the applying and/or contacting may be effected by energy input, in particular by stirring and/or ultrasonication. This serves to further improve the penetration of the solution/dispersion into the pore system of the activated carbon. The catalytically active component should in this respect be employed in this context in the form of a solution/dispersion, particularly as defined above. The applying/contacting may equally be effected, under reduced and/or superatmospheric pressure. The above remarks may also be referenced for this.

In this context, it is advantageous for the purposes of the present invention when particularly after the applying and/or contacting and/or particularly for the purposes of endowing/loading/coating/impregnating the oxidized, specifically surface oxidized, activated carbon with the catalytically active component, in particular in step (c), excess amounts of catalytically active component, in particular excess amounts of solution and/or dispersion of the catalytically active component, can be removed and/or separated from the activated carbon and/or the catalyst system. This may be done on the basis of methods known per se to a person skilled in the art, examples being dripping off or separating off in an air stream or the like.

The method of the present invention may further provide that particularly after the applying/contacting and/or particularly for the purposes of endowing/loading/coating/impregnating the oxidized, specifically surface oxidized, activated carbon with the catalytically active component (and optionally after excess amounts of catalytically active component have been separated off), the activated carbon obtained is cleaned up/dried, in particular after step (c) and/or in particular before step (d) of the method according to the present invention.

In this context, the cleanup/drying should be effected using at least one washing operation in a liquid, in particular water. Similarly, the cleanup/drying should be effected by heating the activated carbon endowed with the catalytically active component, in particular to temperatures in the range from 40° C. to 200° C., in particular 50° C. to 150° C., preferably 60° C. to 120° C. Similarly the clean up and/or drying is carried out under reduced (air) pressure and/or in vacuo and/or in particular wherein the clean up/drying is effected at an (air) pressure in the range from 100 Pa to 0.01 Pa, in particular 10 Pa to 0.1 Pa.

As noted above, the removal of solvent/dispersant medium, i.e., drying the activated carbon, leads to the formation of a reactive catalytic component present in dried/particulate form, particularly in crystalline form, at/on the surfaces of the activated carbon employed as catalyst carrier.

The method of the present invention provides in general that not only the outer but also the inner surfaces, in particular the micro-, meso- and/or macropores, of the oxidized, specifically surface-oxidized activated be endowed/loaded/coated/impregnated with the catalytically active component.

The reduction particularly in step (d) of the catalyst material thus obtained may further be effected by using at least one liquid and/or gaseous reducing agent, in particular gaseous reducing agents, preferably hydrogen. Useful reducing agents in principle also include formalin, hydrazine and also complex hydrides, such as $LiAlH_4$ and/or $NaBH_4$.

The reduction, effected in a preferred embodiment of the present invention, of the resulting activated carbon endowed with the catalytically active component particularly in dried/particulate/crystalline form and/or of the present catalyst system as such is believed—without wishing to be limited to this theory—to lead to a removal/reduction of specifically oxygen-containing functional groups on the surface including that of the pore system of the activated carbon (surface reduction), thereby so to speak effecting a neutral surface and/or a neutralization of the catalyst material and/or of the underlying activated carbon. In consequence, the thus treated catalyst system of the present invention and/or the corresponding activated carbon also convinces a reduced level of inherent reactivity due to the reduced level of functional groups at the surface thereof, something which is conducive to the catalytic property as a whole. In addition, the optionally performed reduction of the present invention reduces the hydrophilicity of the activated carbon and/or the level of polar groups, which serves to improve the penetration behavior of specifically hydrophobic and, respectively, apolar reactants/starting materials.

In addition, the optionally performed reductive treatment may—again without wishing to be limited to this theory—also lead to an at least partial reduction of the catalytically active component imported into/atop the activated carbon. More particularly, the underlying metal compound/component, preferably the corresponding metal, may be reduced in this way, in particular when the catalytically active component or the metal component is present in the form of salts, ions or the like. The reductive treatment may thus generally also be carried out against the background of an optionally desired catalyst activation and/or conversion of the catalyst and/or catalytically active component in active form, in particular by changing and/or reducing the oxidization number of the metal of the catalytically active component.

The reductive treatment, as noted above, may be carried out with preference in the case of noble metals not in the oxidation state of zero and/or the form of a compound, in particular in the form of salt, when employed for example in the context of endowing and/or loading and/or coating and/or impregnating activated carbon with the catalytically active component, i.e. in step (c), such that a corresponding conversion of the noble metal is effected in the elemental form and/or in the oxidation state of zero, so as to thereby realize/effect a catalyst activation and/or a conversion into the catalytically active form.

The present invention may provide that reduction of the catalyst material is effected in an atmosphere containing the reducing agent, in particular hydrogen, in particular in an inert atmosphere, preferably a nitrogen atmosphere. In this context, the atmosphere may contain the reducing agent, particularly hydrogen, in amounts ranging from 0.1 vol % to 20 vol %, in particular 0.5 vol % to 10 vol %, preferably 1 vol % to 5 vol %, based on the volume of the atmosphere. For example, the reduction may be carried out in a flow tube or the like by establishing a defined level of volume flow.

The present invention may accordingly provide overall that the resulting catalyst system according to the invention, and/or the activated carbon endowed with the catalytically active component, be subjected to a reductive treatment in step (d) in particular.

This reduction of the catalyst system in step (d) with preference may be effected at temperatures in the range from 0° C. to 750° C., in particular 20° C. to 700° C., preferably 50° C. to 650° C., more preferably 100° C. to 500° C., even more preferably 200° C. to 400° C. More particularly, the reduction of the catalyst system may be effected at a 5 l/h to 1000 l/h, in particular 10 l/h to 500 l/h, preferably 50 l/h to 300 l/h, volume flow of the atmosphere containing the reducing agent.

The catalyst system as such, obtained in particular by the method according to the present invention, and/or the activated carbon loaded with the catalytically active component in particular may include the catalytically active component in amounts of 0.001 wt %, in particular at least 0.01 wt %, preferably at least 0.5 wt %, more preferably at least 1 wt %, yet more preferably at least 2 wt %, most preferably at least 3 wt %, reckoned as metal and based on the total weight of the catalyst system and/or of the activated carbon endowed with the catalytically active component.

Especially the catalyst system and/or the activated carbon may include the catalytically active component in amounts of at most 10 wt %, in particular at most 15 wt %, preferably at most 20 wt %, more preferably at most 25 wt %, yet more preferably at most 30 wt %, reckoned as metal and based on the total weight of the catalyst system and/or of the activated carbon endowed with the catalytically active component.

In this context, the catalyst system and/or the activated carbon may include the catalytically active component in amounts ranging from 0.001 wt % to 30 wt %, in particular 0.01 wt % to 25 wt %, preferably 0.5 wt % to 20 wt %, more preferably 1 wt % to 15 wt %, yet more preferably 2 wt % to 10 wt %, reckoned as metal and based on the total weight of the catalyst system and/or of the activated carbon endowed with the catalytically active component. The aforementioned amounts relate in particular also to the entirety of the catalytically active component(s) in the catalyst system and/or of the activated carbon.

In this context, therefore, mixtures and/or a plurality of catalytically active components may also be employed for the purposes of the present invention. The present invention may accordingly provide that the catalyst system of the present invention should include a multiplicity of mutually different catalytically active components, in particular as defined above, preferably two, three or four or more mutually different catalytically active components. More particularly, the respective catalytically active components may be present in the catalyst system/activated carbon in an amount ranging from 0.001 to 5 wt %, reckoned as metal and based on the total weight of the catalyst system and/or of the activated carbon endowed with the catalytically active component.

The metal component content of the adsorption material is quantifiable on the basis of elemental analyses for example. The underlying techniques are well known to a person skilled in the art, so no further elucidation is required on this.

With regard to the catalyst system obtained in the context of the method according to the present invention, particularly in the form of the end/ready-to-use product, it is preferable for the purposes of the present invention for the catalyst system/activated carbon to include the catalytically active component at least to some extent in corpuscle form and/or in particulate form, in particular in crystalline form, preferably in the form of crystallites.

In this context, the corpuscles/particles, in particular the crystallites, of the catalytically active component may have an average corpuscle and/or particle size, in particular an average crystallite size, in the range from 0.001 nm to 500 nm, in particular 0.01 nm to 400 nm, preferably in the range from 0.1 nm to 200 nm, more preferably in the range from 0.5 nm to 100 nm, yet more preferably in the range from 1 nm to 50 nm, most preferably in the range from 2 nm to 20 nm.

The corresponding quantification of the corpuscle/crystallite sizes may utilize techniques which in this context are per se well known to a person skilled in the art, such as x-ray diffractometry (XRD) and/or transmission electron microscopy (TEM).

The invention may more particularly provide that the catalytically active component should have a crystallinity, in particular a degree of crystallinity, of at least 10%, in particular at least 30%, preferably at least 50%, more preferably at least 80%, yet more preferably at least 90%, most preferably at least 95%, based on the catalytically active component. More particularly, the catalytically active component may have a crystallinity, in particular a degree of crystallinity, in the range from 10% to 99.5%, in particular in the range from 30% to 99%, preferably in the range from 50% to 98%, more preferably in the range from 80% to 95%.

Therefore, the present invention thus may also provide that the catalytically active component is present in the underlying activated carbon in partially crystalline form. If desired, the catalytically active component may also be present in amorphous form.

By virtue of the amounts of catalytically active component being adjustable according to the present invention as well as the catalytically active component's corpuscle size and the underlying degree of crystallinity, the catalyst system of the present invention may with regard to its catalytic properties be further custom-tailored and/or individually fine-tuned against the particular service background. More particularly, the concept of the present invention—by establishing the parameters within the aforementioned ranges—also ensures that the pore system of the activated carbon endowed with the catalytically active component does not plug, at least essentially, and therefore is at least essentially free to be accessed by reactants or starting materials to be converted catalytically.

The parametric data recited hereinbelow with regard to the underlying activated carbon used/present in the context of the method according to the present invention are determined by means of standardized or explicitly reported methods of determination or by using methods of determination which are per se familiar to those skilled in the art. Especially the parametric data relating to the characterization of the porosity, of the pore size distribution and other adsorptive properties are generally each obtained from the corresponding nitrogen sorption isotherm of the particular activated carbon and/or the products measured. The parameters reported for the initial activated carbon are correspondingly also found in the activated carbon endowed with the catalytically active component.

More particularly, the catalyst system/activated carbon may have a particle size, in particular a corpuscle diameter, in the range from 0.05 mm to 2 mm, in particular 0.05 mm to 1 mm, preferably 0.06 mm to 0.8 mm, preferably 0.07 mm to 0.7 mm, yet more preferably 0.08 mm to 0.6 mm, most preferably 0.08 mm to 0.2 mm. In this connection, the invention may provide that at least 80 wt %, in particular at least 90 wt %, preferably at least 95 wt % of the activated carbon particles, in particular activated carbon corpuscles, have particle sizes, in particular corpuscle diameters, in the aforementioned ranges.

In addition, the catalyst system and/or activated carbon may have a median particle size (D50), in particular a median corpuscle diameter (D50), in the range from 0.05 mm to 1 mm, in particular 0.05 mm to 0.8 mm, preferably 0.06 mm to 0.6 mm, more preferably 0.07 mm to 0.5 mm, yet more preferably 0.08 mm to 0.2 mm.

The corresponding diameters/particle sizes are determinable on the basis of the ASTM D2862-97/04 method in particular. In addition, the aforementioned sizes can be determined with methods of determination which are based on a sieve analysis, x-ray diffraction, laser defractometry, or the like. The particular methods of determination are as such well known to those skilled in the art, so no further elaboration is needed in this regard.

More particularly, the catalyst system and/or the activated carbon may have a tapped and/or tamped density in the range from 100 g/l to 1500 g/l, in particular 125 g/l to 1000 g/l, preferably 150 g/l to 800 g/l, more preferably 200 g/l to 600 g/l, yet more preferably 225 g/l to 500 g/l, most preferably 250 g/l to 400 g/l. Tapped/tamped density is quantifiable as per DIN 53194 in particular.

The catalyst system/activated carbon may further have a bulk density in the range from 150 g/l to 1000 g/l, in particular from 250 g/l to 700 g/l, preferably 300 g/l to 600 g/l. The bulk density is quantifiable as per ASTM B527-93/00 in particular:

The catalyst system and/or the activated carbon may additionally have an abrasion resistance (ball pan hardness) and/or abrasion hardness of at least 90%, in particular at least 95%, preferably at least 97%, more preferably at least 98%, yet more preferably at least 99%, yet still more preferably at least 99.5%.

The catalyst system of the present invention and/or the activated carbon are further notable for outstanding mechanical properties, as is also reflected in an outstanding abrasion resistance. As noted above, the high mechanical in-service strength of the catalyst system according to the present invention will lead to but minimal attrition, as is more particularly advantageous with regard to the use and also the avoidance of sludge formation due to attrition or the like. Abrasion resistance is generally quantifiable as per ASTM D3802-05.

In addition, the catalyst system/activated carbon may have a total pore volume that is, in particular a Gurvich total pore volume, in the range from 0.1 cm$^3$/g to 4 cm$^3$/g, in particular 0.2 cm$^3$/g to 3.5 cm$^3$/g, preferably 0.5 cm$^3$/g to 3 cm$^3$/g, more preferably 0.7 cm$^3$/g to 2.5 cm$^3$/g, most preferably 1 cm$^3$/g to 2 cm$^3$/g. In this context, 30% to 99%, in particular 40% to 99%, preferably 50% to 95%, of the total pore volume, in particular of the Gurvich total pore volume, of the catalyst system and/or of the activated carbon is formed by pores having pore diameters of 50 nm, in particular by micro- and/or mesopores. Similarly 10% to 85%, in particular 20% to 80%, preferably 30% to 75%, of the total pore volume, in particular of the Gurvich total pore volume, of the catalyst system and/or of the activated carbon may be formed by pores having pore diameters in the range from 2 nm to 50 nm, in particular by mesopores.

The Gurvich determination of total pore volume is a method of measurement/determination which is well known per se to a person skilled in the art. For further details regarding the Gurvich determination of total pore volume, reference can be made for example to L. Gurvich (1915), J. Phys. Chem. Soc. Russ. 47, 805, and also to S. Lowell et al., Characterization of Porous Solids and Powders: Surface Area Pore Size and Density, Kluwer Academic Publishers, Article Technology Series, pages 111 ff. More particularly, the pore volume of activated carbon may be determined on the basis of the Gurvich rule as per the formula $V_P = W_a/\rho_I$, where $W_a$ is the adsorbed quantity of an underlying adsorbate and $\rho_I$ is the density of the adsorbate employed (cf. also formula (8.20) as per page 111, chapter 8.4) of S. Lowell et al.).

More particularly, the catalyst system or the activated carbon may include a pore volume formed by pores having pore diameters ≤2 nm, in particular a carbon black micropore volume, in the range from 0.05 cm$^3$/g to 2 cm$^3$/g, in particular 0.1 cm$^3$/g to 1.5 cm$^3$/g, preferably 0.2 cm$^3$/g to 1.2 cm$^3$/g, more preferably 0.3 cm$^3$/g to 1.1 cm$^3$/g, most preferably 0.7 cm$^3$/g to 1 cm$^3$/g. In this context, 10% to 95%, in particular 20% to 95%, preferably 30% to 90%, of the total pore volume of the catalyst system and/or of the activated carbon may be formed by pores having pore diameters of ≤2 nm, in particular by micropores.

The carbon black method of determination is known per se to one skilled in the art, so no further details need to be provided here in this regard. In addition, for further details of the carbon black method of determination of determining the pore surface area and the pore volume, reference may be made for example to R. W. Magee, Evaluation of the External Surface Area of Carbon Black by Nitrogen Adsorption, Presented at the Meeting of the Rubber Division of the American Chem. Soc., October 1994, as cited in, for example: Quantacrhome Instruments, AUTOSORB-1, AS1 WinVersion 1.50, Operating Manual, OM, 05061, Quantachrome Instruments, 2004, Florida, USA, pages 71 ff. More particularly, a t-plot may be used to analyze the data.

The invention may provide in particular that the catalyst system/activated carbon has a specific BET surface area in the range from 500 m$^2$/g to 3500 m$^2$/g, in particular 600 m$^2$/g to 3000 m$^2$/g, preferably 700 m$^2$/g to 2750 m$^2$/g, more preferably 800 m$^2$/g to 2500 m$^2$/g, yet more preferably 1200 m$^2$/g to 2500 m$^2$/g, yet still more preferably 1700 m$^2$/g to 2500 m$^2$/g.

The catalyst system and/or activated carbon may further have a surface area formed by micropores which is in the range from 400 to 2500 m$^2$/g, in particular 500 to 2300 m$^2$/g, preferably 600 to 2100 m$^2$/g, more preferably 700 to 1900 m$^2$/g.

The catalyst system and/or activated carbon may further have a surface area formed by mesopores which is in the range from 300 to 2200 m$^2$/g, in particular 400 to 2100 m$^2$/g, preferably 500 to 2000 m$^2$/g, more preferably 600 to 1900 m$^2$/g.

Determining the specific surface area as per BET is in principle known per se to a person skilled in the art, so no further details need be provided here in this regard. All BET surface areas reported/specified relate to the determination as per ASTM D6556-04. In the context of the present invention, the so-called MultiPoint BET method of determination (MP-BET) in a partial pressure range p/p$_0$ of 0.05 to 0.1 is used to determine the BET surface area in general and unless hereinbelow expressly stated otherwise.

In respect of further details regarding the determination of the BET surface area and of the BET method, reference can be made to the aforementioned ASTM D6556-04 standard and also to Rompp Chemielexikon, 10$^{th}$ edition, Georg Thieme Verlag, Stuttgart/New York, head word: "BET-Methode", including the references cited there, and to Winnacker-Küchler (3rd edition), volume 7, page 93 ff. and also to Z. Anal. Chem. 238, pages 187 to 193 (1968).

It has been found to be particularly advantageous to employ a micro/mesoporous but also preferably a mesoporous activated carbon as carrier material for the purposes of the present invention. This is because this makes it possible to realize particularly high levels of loading in relation to the catalytically active component while additionally improving the penetration behavior into the activated carbon of media/liquids containing reactants/starting materials to be converted catalytically, which altogether leads to enhanced catalytic conversions. More particularly, the specific alignment/selection of pore sizes serves to avoid prematurely limiting the mass transfer of the activated carbon inside as well as outside.

Overall, the pore distribution of the activated carbon is very important with regard to the catalytic activity/efficiency of the catalyst system according to the present invention, including in particular also with regard to the degree of loading with the catalytic active component and also the accessibility of the catalyst system to reactants/starting materials. Therefore, the distribution of the pores, i.e., the proportion of the total pore volume which is accounted for by micro-, meso- and macropores, is of similar importance; more particularly, the porosity is precisely controllable through the selection of the starting materials and through the processing conditions.

In the context of the present invention, the term "micropores" refers to pores with pore diameters of less than 2 nm, whereas the term "mesopores" refers to pores having pore diameters in the range from 2 nm (i.e., 2 nm inclusive) up to 50 nm inclusive, and the term "macropores" refers to pores having pore diameters of more than 50 nm (i.e., >50 nm).

In addition, the catalyst system/activated carbon may have an average pore diameter in the range from 0.8 nm to 60 nm, in particular 1 nm to 50 nm, preferably 1.2 nm to 40 nm, more preferably 1.4 nm to 30 nm, yet more preferably 1.6 nm to 20 nm, yet still more preferably 1.8 nm to 10 nm, most preferably 2 nm to 6 nm.

The average pore diameter may be determined from the quotient formed by dividing the BET surface area into four times the volume of a liquid adsorbed/taken up by the activated carbon (adsorbate) with completely filled pores (V$_{total}$) (pore diameter d=4·V$_{total}$/BET). For this, reference may be made to the corresponding explanations offered by R. W. Magee (loc. cit.), in particular to the formula diagram (15) on page 71 of the cited reference.

The abovementioned high mechanical stability of the catalyst system according to the present invention and/or of the activated carbon is also reflected in a high compressive/bursting strength (weight-bearing capacity per activated carbon grain). In this context, the catalyst system/activated carbon may have a compressive and/or bursting strength (weight-bearing capacity) per activated carbon grain, in particular per activated carbon spherule, of at least 5 newtons, in particular at least 10 newtons, preferably at least 15 newtons, more preferably at least 20 newtons. More particularly the catalyst system and/or the activated carbon has a compressive and/or bursting strength (weight-bearing capacity) per activated carbon grain, in particular per activated carbon spherule, in the range from 5 to 50 newtons, in particular 10 to 45 newtons, preferably 15 to 40 newtons.

Compressive/bursting strength may be determined in a manner known per se to a person skilled in the art, in particular by determining the compressive/bursting strength of individual particles/corpuscles via application of force with a ram until the respective particle/corpuscle bursts.

The method of the present invention and also the catalyst system obtainable therewith are associated with a multiplicity of advantages as already itemized above. By virtue of the outstanding catalytic properties of the catalyst system which is in accordance with the present invention and is obtainable using the method of the present invention, a broad service/use spectrum is possible, as will be further detailed hereinbelow.

The present invention—according to a second aspect of the present invention—thus also further provides the catalyst system of the present invention, in particular the supported catalyst, wherein the catalyst system includes at least one catalytically active component on a catalyst carrier, in particular at least one catalytically active component fixed to a catalyst carrier, wherein the catalyst system of the present invention is obtainable as per the above-described method according to the invention.

According to this aspect of the present invention, the present invention similarly provides the catalyst system of the present invention, in particular the supported catalyst of the present invention, wherein the catalyst system includes at least one catalytically active component on a catalyst carrier, in particular at least one catalytically active component fixed to a catalyst carrier, wherein the catalytically active component comprises and/or consists of at least one metal, wherein the catalyst system is obtainable by oxidation, specifically surface oxidation, of a spherical activated carbon employed as catalyst carrier and subsequent endowing and/or loading and/or coating and/or impregnating of the resulting oxidized, specifically surface oxidized, activated carbon with the catalytically active component, in particular by applying, preferably fixing, the catalytically active component to the catalyst carrier, optionally followed by a reduction of the catalyst system thus obtained.

The present invention under this invention aspect additionally also provides the catalyst system according to the invention, in particular the supported catalyst according to the invention, wherein the catalyst system includes at least one catalytically active component on a catalyst carrier, in particular at least one catalytically active component fixed to a catalyst carrier, wherein the catalytically active component comprises and/or consists of at least one metal, and wherein the catalyst carrier is based on activated carbon. The catalyst system or the supported catalyst according to the invention is notable in that the catalyst support or the supported catalyst is present in the form of an at least essentially spherical activated carbon, and in that the applying of the catalytically active component to the activated carbon, in particular the fixing of the catalytically active component to and/or on the activated carbon, is effected while the activated carbon is in an oxidized form.

The invention may more particularly provide that the activated carbon is specifically surface oxidized for the step of applying, in particular fixing, the catalytically active component. This oxidation, in particular surface oxidation, of the activated carbon is effected by use and/or in the presence of at least one oxidizing agent. Similarly, the activated carbon is an oxidized, specifically surface oxidized, activated carbon, in particular before the step of applying, in particular fixing, the catalytically active component.

The present invention may similarly provide that the catalyst system is specifically surface reduced after the step of applying, in particular fixing, the catalytically active component. This reduction of the catalyst system and/or of the activated carbon is effected by use and/or in the presence of at least one reducing agent. More particularly, the activated carbon is reduced, specifically surface reduced, in particular after the step of applying, in particular fixing, the catalytically active component. More particularly, the catalyst system of the present invention may be in particular a surface reduced catalyst system. The present invention may thus provide in this context that the catalyst system or the activated carbon is a reduced catalyst system or, respectively, activated carbon.

More particularly, the reduction of the catalyst system and/or the activated carbon is effected by use and/or in the presence of at least one reducing agent.

In general, the activated carbon may be obtainable. by carbonizing and subsequently activating a starting material based on organic polymers, followed by an oxidation or oxidative treatment, wherein the oxidation or oxidative treatment is effected before applying, in particular fixing, the catalytically active component, and optionally followed by a reduction or reductive treatment, wherein the reduction or reductive treatment is carried out after applying, in particular fixing, the catalytically active component.

The present invention may additionally provide that the activated carbon is obtained from a starting material based on organic polymers, in particular based on sulfonated organic polymers, preferably based on divinylbenzene-crosslinked polystyrene, more preferably based on styrene-divinylbenzene copolymers, in particular by carbonizing and subsequently activating the starting material.

The present invention may additionally provide that the activated carbon is obtained by carbonizing a starting material, in particular organic polymers, preferably sulfonated organic polymers, preferably based on divinylbenzene-crosslinked polystyrene, more preferably based on styrene-divinylbenzene copolymers, and subsequently activating the carbonized starting material.

In this regard, the divinylbenzene content of the starting material may be in the range from 1 wt % to 20 wt %, in particular 1 wt % to 15 wt %, preferably 1.5 wt % to 12.5 wt %, more preferably 2 wt % to 10 wt %, based on the starting material.

In the context of the present invention, the starting material may be of the gel type or of the macroporous type, in particular of the gel type.

More particularly, the catalyst carrier may be a polymer-based spherical activated carbon (PBSAC) and/or the activated carbon may be a polymer-based spherical activated carbon (PBSAC).

It is further advantageous for the purposes of the present invention when the catalytically active component includes and/or consists of at least one metal, in particular in the form of a metal compound, preferably in the form of an ionic metal compound, and/or in particular in elemental form.

The catalytically active component may further include at least one metal in a positive oxidation state, in particular at least one metal cation. In this context, the oxidation state of the metal may reside in the range from +I to +VII, in particular in the range from +I to +IV, preferably in the range from +I to +III, and is more preferably +I or +II. It may further be provided in the context of the present invention that the catalytically active component includes at least one metal having the oxidation state/number of zero.

More particularly, the catalytically active component may include at least one metal from the main or transition groups of the Periodic Table or at least one lanthanide.

According to the present invention, the catalytically active component may include at least one metal selected from elements of main group IV or of transition groups I, II, III, IV, V, VI, VII and VIII of the periodic table, in particular from elements of main group IV or of transition groups I and II of the periodic table.

More particularly, the catalytically active component may include at least one metal selected from the group of Cu, Ag, Au, Zn, Hg, Sn, Ce, Ti, Zr, V, Nb, Cr, Mo, W, Mn, Fe, Bi, Ru, Os, Co, Rh, Re, Ir, Ni, Pd and Pt, in particular Fe, Bi, V, Cu, Pb, Zn, Ag, Sn, Pd, Pt, Ru and Ni, preferably Fe, Bi, V, Cu, Pt, Ru and Pb, more preferably Pd, Pt and Ru.

In addition, the catalytically active component may include at least one organic or inorganic metal compound, preferably based on at least one above-defined metal, in particular a metal salt or metal oxide, preferably a metal salt.

It may additionally be provided according to the present invention that the catalytically active component include at least one organic or inorganic metal salt, preferably based on at least one above-defined metal, wherein the salt is selected from the group of halide salts, sulfates, sulfides, sulfites, nitrates, nitrites, phosphates, phosphides, phosphites, carbamates, alkoxides and carboxylic acid salts, in particular halide salts and carboxylic acid salts.

It is advantageous for the purposes of the present invention when the catalytically active component includes at least one metal halide, preferably based on at least one above-defined metal, in particular a fluoride, chloride, bromide or iodide, preferably chloride, and/or at least one carboxylic acid salt of a metal, preferably based on at least one above-defined metal, in particular acetate.

More particularly, the catalytically active component may include at least one metal compound selected from the group of palladium chloride, hexachloroplatinic acid, ruthenium chloride, copper chloride, iron chloride, vanadium chloride, and lead chloride, in particular palladium chloride, hexachloroplatinic acid, ruthenium chloride.

More particularly, the present invention provides in particular that not only the outer but also the inner surfaces, in particular the micro-, meso- and/or macropores, of the activated carbon and/or the catalyst system are endowed and/or loaded and/or coated and/or impregnated with the catalytically active component.

In this context it is advantageous for the present invention when the catalyst system and/or the activated carbon include the catalytically active component in amounts of at least 0.001 wt %, in particular at least 0.01 wt %, preferably at least 0.5 wt %, more preferably at least 1 wt %, yet more preferably at least 2 wt %, most preferably at least 3 wt %, reckoned as metal and based on the total weight of the catalyst system and/or of the activated carbon endowed with the catalytically active component.

More particularly the catalyst system and/or the activated carbon may include the catalytically active component in amounts of at most 10 wt %, in particular at most 15 wt %, preferably at most 20 wt %, more preferably at most 25 wt %, yet more preferably at most 30 wt %, reckoned as metal and based on the total weight of the catalyst system and/or of the activated carbon endowed with the catalytically active component.

In addition the catalyst system and/or the activated carbon may include the catalytically active component in amounts ranging from 0.001 wt % to 30 wt %, in particular 0.01 wt % to 25 wt %, preferably 0.5 wt % to 20 wt %, preferably 1 wt % to 15 wt %, yet more preferably 2 wt % to 10 wt %, reckoned as metal and based on the total weight of the catalyst system and/or of the activated carbon endowed with the catalytically active component.

More particularly, the catalyst system and/or the activated carbon should include the catalytically active component at least partly in corpuscle form and/or in particulate form, in particular in crystalline form, preferably in the form of crystallites.

In this connection, it is advantageous for the purposes of the present invention when the corpuscles and/or particles, in particular the crystallites, of the catalytically active component have an average corpuscle and/or particle size, in particular an average crystallite size, in the range from 0.001 nm to 500 nm, in particular 0.01 nm to 400 nm, preferably in the range from 0.1 nm to 200 nm, more preferably in the range from 0.5 nm to 100 nm, yet more preferably in the range from 1 nm to 50 nm, most preferably in the range from 2 nm to 20 nm.

The invention may in this context provide that the catalytically active component should have a crystallinity, in particular a degree of crystallinity, of at least 10%, in particular at least 30%, preferably at least 50%, more preferably at least 80%, yet more preferably at least 90%, most preferably at least 95%, based on the catalytically active component. More particularly, the catalytically active component may have a crystallinity, in particular a degree of crystallinity, in the range from 10% to 99.5%, in particular in the range from 30% to 99%, preferably in the range from 50% to 98%, more preferably in the range from 80% to 95%.

Regarding the catalyst system as such and/or the activated carbon as such, the invention may provide that the catalyst system and/or the activated carbon has a particle size, in particular a corpuscle diameter, in the range from 0.05 mm to 2 mm, in particular 0.05 mm to 1 mm, preferably 0.06 mm to 0.8 mm, preferably 0.07 mm to 0.7 mm, yet more preferably 0.08 mm to 0.6 mm, most preferably 0.08 mm to 0.2 mm. In this connection at least 80 wt %, in particular at least 90 wt %, preferably at least 95 wt % of the particles, in particular corpuscles, have particle sizes, in particular corpuscle diameters, in the aforementioned ranges.

The present invention may provide that the catalyst system and/or the activated carbon has a median particle size (D50), in particular a median corpuscle diameter (D50), in the range from 0.05 mm to 1 mm, in particular 0.05 mm to 0.8 mm, preferably 0.06 mm to 0.6 mm, more preferably 0.07 mm to 0.5 mm, yet more preferably 0.08 mm to 0.2 mm.

In addition, the catalyst system and/or the activated carbon may have a tapped and/or tamped density in the range from 100 g/l to 1500 g/l, in particular 125 g/l to 1000 g/l, preferably 150 g/l to 800 g/l, more preferably 200 g/l to 600 g/l, yet more preferably 225 g/l to 500 g/l, most preferably 250 g/l to 400 g/l.

In addition, the catalyst system and/or the activated carbon may have a bulk density in the range from 150 g/l to 1000 g/l, in particular from 250 g/l to 700 g/l, preferably 300 g/l to 600 g/l.

More particularly, the catalyst system and/or the activated carbon may have an abrasion resistance (ball pan hardness) and/or abrasion hardness of at least 90%, in particular at least 95%, preferably at least 97%, more preferably at least 98%, yet more preferably at least 99%, yet still more preferably at least 99.5%.

The present invention may additionally provide that the catalyst system and/or the activated carbon has a total pore volume, in particular a Gurvich total pore volume, in the range from 0.1 cm$^3$/g to 4 cm$^3$/g, in particular 0.2 cm$^3$/g to 3.5 cm$^3$/g, preferably 0.5 cm$^3$/g to 3 cm$^3$/g, more preferably 0.7 cm$^3$/g to 2.5 cm$^3$/g, most preferably 1 cm$^3$/g to 2 cm$^3$/g. In this connection 30% to 99%, in particular 40% to 99%, preferably 50% to 95%, of the total pore volume, in particular of the Gurvich total pore volume, of the catalyst system and/or of the activated carbon may be formed by pores having pore diameters of 50 nm, in particular by micro- and/or mesopores. In addition 10% to 85%, in particular 20% to 80%, preferably 30% to 75%, of the total pore volume, in particular of the Gurvich total pore volume, of the catalyst system and/or of the activated carbon may be formed by pores having pore diameters in the range from 2 nm to 50 nm, in particular by mesopores.

More particularly, the catalyst system or the activated carbon may include a pore volume formed by pores having pore diameters ≤2 nm, in particular a carbon black micropore volume, in the range from 0.05 cm$^3$/g to 2 cm$^3$/g, in particular 0.1 cm$^3$/g to 1.5 cm$^3$/g, preferably 0.2 cm$^3$/g to 1.2 cm$^3$/g, more preferably 0.3 cm$^3$/g to 1.1 cm$^3$/g, most preferably 0.7 cm$^3$/g to 1 cm$^3$/g. In this context, 10% to 95%, in particular 20% to 95%, preferably 30% to 90%, of the total pore volume of the catalyst system and/or of the activated carbon may be formed by pores having pore diameters of ≤2 nm, in particular by micropores.

In addition, the catalyst system and/or the activated carbon may have a specific BET surface area in the range from 500 m$^2$/g to 3500 m$^2$/g, in particular 600 m$^2$/g to 3000 m$^2$/g, preferably 700 m$^2$/g to 2750 m$^2$/g, more preferably 800 m$^2$/g to 2500 m$^2$/g, yet more preferably 1200 m$^2$/g to 2500 m$^2$/g, yet still more preferably 1700 m$^2$/g to 2500 m$^2$/g.

More particularly the catalyst system and/or activated carbon may have a surface area formed by micropores which is in the range from 400 to 2500 m$^2$/g, in particular 500 to 2300 m$^2$/g, preferably 600 to 2100 m$^2$/g, more preferably 700 to 1900 m$^2$/g.

It may similarly be provided in the context of the present invention that the catalyst system and/or the activated carbon should have an average pore diameter in the range from 0.8 nm to 60 nm, more preferably 1 nm to 50 nm, yet more preferably 1.2 nm to 40 nm, more preferably 1.4 nm to 30 nm, yet more preferably 1.6 nm to 20 nm, yet still more preferably 1.8 nm to 10 nm, most preferably 2 nm to 6 nm.

According to the present invention, the catalyst system and/or the activated carbon may have a compressive and/or bursting strength (weight-bearing capacity) per activated carbon grain, in particular per activated carbon spherule, of at least 5 newtons, in particular at least 10 newtons, preferably at least 15 newtons, more preferably at least 20 newtons. According to the present invention, the catalyst system and/or the activated carbon may especially have a compressive and/or bursting strength (weight-bearing capacity) per activated carbon grain, in particular per activated carbon spherule, in the range from 5 to 50 newtons, in particular 10 to 45 newtons, preferably 15 to 40 newtons.

In summary, the present invention succeeds in overcoming the prior art disadvantages associated with activated carbon additized with catalysts being employed in finely divided form. As noted above, activated carbons comprising a catalyst generally take the form of a finely ground powder in the prior art, in particular in order to control mass transfer limitations in relation to the target reaction desired. However, low particle sizes often lead to an appreciable level of time intensity particularly when it comes to removing the catalyst after its use, as is an indispensible operation with regard to batchwise catalytic processes. This difficulty with separating off the prior art systems is particularly caused by a low bed porosity on the part of the filter cake. As also noted above, while the employment of particulate activated carbon, for example based on coconut shells or on formed carbon, is able to reduce the separation times to a certain extent in the prior art, such particulate activated carbons have a comparatively low mechanical stability, so the underlying carbons are further attrited in the catalysis particularly during the intensive stirring processes.

Against that background, the present inventors found that—utterly surprisingly—the prior art disadvantages are overcome by providing a specific spherical/ball-shaped activated carbon endowed with a catalytically active component.

In this context, the employment of a loading oxidized spherical activated carbon with the catalytically active component is accorded high significance, and in this regard the preference of the present invention is for employing a polymer-based activated carbon. This is because, in this context, the catalyst systems provided according to the present invention are quite surprisingly found not to suffer any significant reduction in catalytic activity due to mass transfer limitation—and this even though the activated carbons employed according to the present invention have large corpuscle diameters as powdered activated carbons. In addition, the separation time of batch processes is distinctly minimized. The exemplary embodiments hereinbelow even evidence an enhanced catalytic activity versus powdered reference catalysts, evidencing the outstanding efficacy on the part of the catalyst systems according to the present invention. This is another way in which the catalyst systems provided by the present invention accordingly lead to an appreciable shortening of processing time, particularly also with regard to batchwise catalytic processes, due to a shortening of separation steps coupled with enhanced catalytic activity. The employment of catalyst systems according to the present invention, which may interchangeably also be referred to as activated carbon supported (noble) metal catalysts, additionally leads to a simplified dosing regime, to distinctly lower cleaning requirements for the underlying apparatuses, to minimized losses of material and also, in general, to a simplified form of handling, all of which is very important also against the background of the cost intensity of catalysts and leads to a significant cost saving.

In addition, the catalyst systems of the present invention are simple to recycle/reuse following appropriate reactivation of the catalyst. More particularly, the pronounced mesoporous system of the activated carbons employed according to the present invention as a carrier material leads to a significant improvement in catalytic activity. Pore systems of this type are not present in other activated carbon systems, such as pitch-based activated carbons or the like. In addition, the catalyst systems of the present invention have a high level of mechanical stability and/or abrasion hardness, which is far superior to that of, for example, pitch-based activated carbons or the like.

The catalyst system of the present invention, in addition to the batchwise use, is also outstandingly suitable for employment in continuous catalytic applications, in that the underlying catalyst systems may for example be filled into appropriate cartridges/reaction vessels and have a medium comprising reactants/starting materials passing through them in a continuous manner, while the use of the catalyst system according to the present invention—in fundamental contradistinction to the employment of powdered carbon—makes it possible to achieve a but low pressure drop at correspondingly high flow rates. In addition, the pressure drop is controllable by precisely adjusting the particle/corpuscle sizes of the catalyst system according to the present invention, in that comparatively small corpuscle/particle sizes tend to lead to comparatively high pressure drops at correspondingly lower flow rates and large corpuscle/particle sizes tend to lead to lower pressure drops and higher flow rates, so a custom-tailored catalyst system is also obtainable in this way according to the present invention.

As noted above, the catalyst system of the present invention has a broad spectrum of application. In addition to its use in catalysis, in particular on an industrial scale, the catalyst system of the present invention is particularly by virtue of its combined properties of chemisorption on the one hand and physisorption on the other also suitable for (ad)sorptive purposes, for example to remove toxic substances, such as noxiant or poisonous materials.

The present invention—in accordance with a third aspect of the present invention—thus further also provides for the methods of using the catalyst system of the invention in the manner of the invention. For instance, the catalyst system of the present invention is useful in the manufacture of filters and filter materials, in particular for removal of noxiant, odorant and poisonous materials, in particular from air and/or gas streams, such as NBC respirator filters, odor filters, sheet filters, air filters, in particular filters for room air cleaning, adsorption-capable and/or chemisoprtion-capable carrier structures and filters for the medical sector.

The catalyst system of the present invention is further useful as sorption store for gases or liquids.

The catalyst system of the present invention is additionally useful as a catalyst or catalyst carrier.

The catalyst system of the present invention additionally has high suitability for chemical catalysis, in particular for heterogeneous catalysis, and/or for batchwise or continuous catalysis.

In this context, the catalyst system of the present invention may be used for example to catalyze chemical processes and reactions, in particular oligomerization and polymerization reactions, preferably of olefins, or hydrogenation reactions.

The catalyst system according to the invention is similarly useful in or as gas sensors or in fuel cells. The catalyst system according to the invention is additionally useful for sorptive, specifically adsorptive and/or chemisorptive, applications, preferably chemisorptive applications, in particular as a preferably reactive/catalytic adsorbent.

The catalyst system according to the invention is also useful for gas cleaning and/or gas conditioning.

The catalyst system of the present invention is more particularly useful for the removal of noxiants, in particular gaseous noxiants, or of toxic, hazardous or environmentally harmful substances or gases. In addition, the present invention contemplates using the catalyst system of the invention for conditioning and/or providing cleanroom atmospheres, in particular for the electrical/electronics industry, in particular for semiconductor or chip manufacture.

The present invention—in accordance with a fourth aspect of the present invention—more particularly provides protective materials, in particular for the civilian or military sector, in particular protective apparel, such as protective suits, protective gloves, protective footwear, protective socks, protective headwear, and also protective coverings, preferably any aforementioned protective material for NBC deployment, obtained by using the catalyst system of the present invention or including the catalyst system of the present invention.

The present invention—in accordance with a fifth aspect of the present invention—additionally further provides filters and filter materials, in particular for removal of noxiant, odorant and poisonous materials, in particular from air and/or gas streams, such as NBC respirator filters, odor filters, sheet filters, air filters, in particular filters for room air cleaning, adsorption-capable carrier structures and filters for the medical sector, obtained by using an above-defined catalyst system or including a previously defined catalyst system of the present invention.

The filters and filter materials of the present invention may be varied in their construction:

The invention may for instance provide that the catalyst system is self-supporting and/or in the form of a specifically loose bed.

Alternatively, the present invention may also provide that the catalyst system is supported by a carrier material.

In this context, the invention may provide that the carrier material may be gas permeable, in particular air permeable.

For this eventuality, the invention may provide that the carrier material has a gas permeability, in particular air permeability, of at least 10 $l \cdot m^{-2} \cdot s^{-1}$, in particular at least 30 $l \cdot m^{-2} \cdot s^{-1}$, preferably at least 50 $l \cdot m^{-2} \cdot s^{1}$, more preferably at least 100 $l \cdot m^{-2} \cdot s^{-1}$, most preferably at least 500 $l \cdot m^{-2} \cdot s^{-1}$, and/or a gas permeability, in particular air permeability, of up to 10 000 $l \cdot m^{-2} \cdot s^{-1}$, in particular up to 20 000 $l \cdot m^{-2} \cdot s^{-1}$, at a flow resistance of 127 Pa.

For this eventuality, it may be similarly provided moreover that the carrier material has a three-dimensional structure. In this respect, the carrier material may be configured as a preferably open-pore foam, more preferably as a polyurethane foam.

In the case of the carrier material being implemented in two-dimensional form, the invention may provide that the carrier material be configured as a textile fabric, preferably an air-permeable textile material, more preferably as a woven, loop-formingly knitted, loop-drawingly knitted, blade or bonded fabric, in particular as a nonwoven. More particularly, the carrier material may have a basis weight of 5 to 1000 $g/m^2$, in particular 10 to 500 $g/m^2$, preferably 25 to 450 $g/m^2$.

Particularly in the case of a two-dimensional incarnation of the carrier material, the carrier material may be a textile fabric containing or consisting of natural fibers and/or synthetic fibers (manufactured fibers), in particular wherein the natural fibers are selected from the group of wool fibers and cotton fibers (CO), and/or in particular wherein the synthetic fibers are selected from the group of polyesters (PES); polyolefins, in particular polyethylene (PE) and/or polypropylene (PP); polyvinyl chlorides (CLF); polyvinylidene chlorides (CLF); acetates (CA); triacetates (CTA); acrylics (PAN); polyamides (PA), in particular aromatic, preferably flame-resistant polyamides; polyvinyl alcohols (PVAL); polyurethanes; polyvinyl esters; (meth)acrylates; polylactic acids (PLA); activated carbon; and also mixtures thereof.

The present invention is in effect the first to succeed in providing an effective catalyst system having both outstanding mechanical and catalytic properties.

Further versions, alterations, variations, modifications, special features and advantages of the present invention will be readily apparent to and realizable by the ordinarily skilled on reading the description without their having to go outside the realm of the present invention.

The present invention is illustrated by the following exemplary embodiments which, however, shall in no way limit the present invention.

EXEMPLARY EMBODIMENTS

1. Preparation of Inventive Catalyst Systems Endowed with a Catalytically Active Component The catalyst carrier material employed in the context of the present exemplary embodiments to obtain inventive catalyst systems by endowment with a catalytically active component is a polymer-based spherical activated carbon (PBSAC), said activated carbon having a total pore volume of about 1.2 $cm^3/g$ from a micropore content of about 55 vol % (i.e., it is a micro/mesoporous activated carbon). An initial activated carbon of this type is available from Blüicher GmbH, Erkrath (Germany). The underlying activated carbon further has a tapped density of about 350 g/l, an average corpuscle size of about 0.175 μm, a BET surface area of about 2200 m²/g and also an average pore diameter of about 5 nm.

(i) To prepare inventive catalyst system A1, 5 g of the initial activated carbon are brought together with an HNO₃ solution (10%), and the resulting mixture is stirred for 2.5 h. Excess nitric acid is subsequently separated off. The activated carbon is washed with distilled water to a constant pH and subsequently dried at 120° C. in a vacuum of 10⁻² mbar.

The surface-oxidized activated carbon thus obtained is brought together with a solution of the catalytically active component (PdCl₂), said solution being obtained by combining 29.5 ml of water, 5.5 ml of 1 N hydrochloric acid and 0.42 g of PdCl₂. The resulting mixture is stirred at a defined stirring speed for 24 h. The activated carbon provided the catalytically active component, i.e., the impregnate, is subsequently separated off and washed with distilled water. This is followed by drying at 120° C. in a vacuum of 10⁻² mbar.

The catalyst system thus obtained is subsequently reduced in an H₂/N₂ gas mixture containing 3.5 vol % of H₂, based on the atmospheric volume, in a flow tube at a temperature of 80° C. under a total volume flow of about 100 l/h for a period of 1 h to obtain the inventive catalyst system.

(ii) To prepare inventive catalyst system A2, first an oxidation of the initial activated carbon is carried out using nitric acid and the surface-oxidized activated carbon thus obtained is dried (cf. the above under (i)).

To endow the activated carbon with the catalytically active component, first a solution of the catalytically active component (based on H₂PtCl₆) is prepared by dissolving 1.32 g of H₂PtCl₆ (6H₂O) in 59 ml of H₂O and 11 ml of N hydrochloric acid. Then, 10 g of the oxidized activated carbon are added to this solution, and the mixture thus obtained is stirred for 24 h. This is followed by the activated carbon endowed with the catalytically active component and/or the impregnate being separated off, followed by rinsing with distilled water, in turn followed by drying the treated activated carbon at 120° C. in a vacuum of 10⁻² mbar.

The catalyst system obtained is subsequently subjected to a reduction in a flow tube at about 300° C. by using an H₂/N₂ gas mixture having an H₂ content of 3.5 vol % at a total volume flow of about 100 l/h for a period of 1 h to obtain inventive catalyst system A2.

(iii) Further, to prepare inventive catalyst system A3, 10 g of the underlying activated carbon are brought together with a sulfuric acid solution (50%) and the mixture thus obtained is stirred at a temperature of 90° C. for a period of 2.5 h. Excess oxidizing solution is subsequently separated off and the surface-oxidized activated carbon thus obtained is washed with distilled water to a constant pH. This is followed by drying at about 120° C. under a vacuum of 10⁻² mbar.

To endow the activated carbon thus obtained with the catalytically active component (based on RuCl₃), the underlying activated carbon is subsequently brought together with a solution of the catalytically active component, said solution including 0.56 g of RuCl₃(H₂O), dissolved in 29.5 ml of distilled water and 1100 ml of 1 N hydrochloric acid. The mixture thus obtained is stirred for 24 h. This is followed by the activated carbon endowed with the catalytically active component being separated off and the activated carbon obtained being rinsed with distilled water.

After the activated carbon endowed with the catalytically active component has been dried at 120° C. in vacuo at 10⁻² mbar, the activated carbon endowed with the catalytically active component is reduced in a flow tube at 300° C. by using an H₂/N₂ gas mixture 3.5 vol % of H₂ at a total volume flow of about 100 l/h for a period of 1 h to obtain inventive catalyst system A3.

(iv) To prepare inventive catalyst system A4, exemplary embodiment (i) is repeated in general terms except that the oxidative treatment carried out on the underlying activated carbon is carried out by employing (atmospheric) oxygen as oxidizing agent. To this end, the initial activated carbon is heated in an air stream at 450° C. for a period of 3 h.

(v) Further, to prepare inventive catalyst system A5, exemplary embodiment (i) is repeated except that the oxidation of the initial activated carbon is carried out by employment of hydrogen peroxide (H₂O₂). To this end, the initial activated carbon employed is brought together at room temperature with an H₂O₂ solution (10%), and the mixture thus obtained is stirred for 2.5 h. Excess oxidizing agent is subsequently separated off and the oxidized activated carbon obtained is washed with distilled water to a constant pH.

(vi) In addition, inventive catalyst system A6 is prepared according to inventive example (i) except that the final step of reducing the catalyst system and/or the activated carbon endowed with the catalytically active component is not carried out. Inventive catalyst system A6 accordingly comprises an inventive catalyst system wherein the activated carbon carrier material in the (end) product obtained is present in oxidized form (inventive catalyst material A6).

(vii) Inventive catalyst system A7 is similarly prepared according to exemplary embodiment (ii) except that the activated carbon endowed with the catalytically active component is subsequently not reduced. Inventive activated carbon A7 accordingly comprises an oxidized activated carbon endowed with a catalytically active component in the resulting catalyst system as end product.

2. Preparation of Further Catalyst Systems (Comparative)

A first complex of preparation comprises the preparation of catalyst systems based on a spherical activated carbon as initial activated carbon of the type described above under item 1.). However, the resulting catalyst systems differ from the inventive catalyst systems described under item 1.), particularly to the effect that the loading with the catalytically active component is carried out by using non-oxidized initial activated carbons. Thus, with regard to the subsequent catalyst systems, no oxidizing step is carried out before loading with the catalytically active component. Regarding the corresponding catalyst systems in detail:

(viii) Exemplary embodiment (i) featuring inventive catalyst system A1 as described therein is used as a basis for preparing a corresponding catalyst system except that, as previously noted, no oxidative treatment is carried out before loading with the catalytically active component. The result is a catalyst system B1 based on an activated carbon not oxidized even in the course of loading with the catalytically active component.

(ix) Exemplary embodiment (ii) featuring catalyst system A2 as described therein is repeated to prepare a corresponding catalyst system B2 except that, similarly, no oxidation of the activated carbon is carried out before loading with the catalytically active component.

(x) Lastly, a catalyst system B3 is provided in line with exemplary embodiment (iii) and the catalyst system described therein. Catalyst system B3 thus likewise comprises a catalyst system wherein the activated carbon functioning as carrier material is not subjected to an oxidizing reaction before being loaded/endowed with the catalytically active component.

A further (comparative) catalyst system is additionally prepared from a different type of initial activated carbon, as described in what follows:

(xi) (Comparative) catalyst system B4 is prepared employing an activated carbon obtained by corresponding processing of coconut shells as starting material. The coconut shell based activated carbon is endowed with the catalytically active component employed according to exemplary embodiment (i). The resulting catalyst system comprises a finely divided carbon of the powdered type.

The catalyst systems obtained are subsequently investigated with regard to their corresponding properties, as described in what follows:

3. Preparing Further Inventive Catalyst Systems on the Basis of Different Porosities Inventive activated carbons A8 and A9 are further prepared on the basis of exemplary embodiment (i). However, inventive catalyst systems A8 and A9 utilized PBSAC-based activated carbons having a further increased proportion of mesopores (catalyst system A8) and/or an increased macropore content (catalyst system A9).

4. Investigations/Properties of Inventive Catalyst Systems and of Corresponding Comparative Catalyst Systems 1a. In a first complex of investigations, the catalytic properties of inventive catalyst system A1 are investigated. This is done employing a catalyst system A1 which has a catalyst content of 5 wt %, based on the catalyst system. The reaction investigated is the catalytic hydrogenation of cinnamic acid into hydrocinnamic acid.

To this end, the reaction is carried out in a steel autoclave equipped with a sparging stirrer. The target product in the form of hydrocinnamic acid is sampled and also characterized at defined intervals using gas chromatography and/or coupled gas chromatography and mass spectrometry (GC-MS). A cinnamic acid solution of 0.24 mol/l in 200 ml of ethanol is employed for this.

The amount of employed catalyst is 0.5 g (further reaction parameters: $U_{stirrer}$=1500 rpm, $p_{H2}$=30 bar and also T=40° C.)

Inventive catalyst system A6 (without reductive treatment), the (comparative) catalyst system B1 (without oxidative treatment) and also the catalyst system based on a finely divided/pulverulent activated carbon endowed with a catalytically active component (catalyst system B4) are investigated in corresponding fashion.

FIG. 1 shows the results found in this regard. What is depicted in FIG. 1 is the time course of the formation of hydrocinnamic acid from cinnamic acid by using the catalysts itemized above. As can be seen in FIG. 1, the highest conversion and thus the greatest catalytic activity are obtained for inventive catalyst system A1. Inventive catalyst system A6 achieves lower conversions, meaning that the catalytic activity is lower, but it is still significantly greater than that obtained with non-inventive catalyst system B1. Catalyst systems A1, A6 and also B1 altogether have higher conversions versus reference system B4, with (comparative) catalyst system B1 displaying the lowest increases in catalytic activity versus reference catalyst system B4. FIG. 1 reports the conversion (in %) on the corresponding Y-axis, while the X-axis reports the modified residence time $T_{mod}$, based on the amount of noble metal and the total volume.

1b. In addition and on the lines of the remarks under 1a.), inventive catalyst systems A8 and A9 are investigated in relation to the conversion of cinnamic acid into hydrocinnamic acid. In this context, further increased conversions and thus a further increased catalytic activity are obtained for inventive catalyst system A9 (having a comparatively high mesopore content) as compared with inventive catalyst system A1 (micro/mesoporous activated carbon). Inventive catalyst system A9 (having a comparatively high fraction of macropores) gives lower conversions in relation to catalyst systems A1 and A9 and hence has by comparison a lower catalytic activity which, however, must still be classified as high overall.

2. In a further complex of investigations, further catalyst systems are investigated for the properties regarding the catalytic conversion/hydrogenation of hexanal into hexanol. The employed catalyst systems contain about 5 wt % of catalytically active component, based on the respective catalyst system. In this regard, inventive catalyst system A2 and also inventive catalyst system A7 are investigated in a comparison against catalyst system B2 (comparative) and catalyst system B4 (comparative).

The reaction is carried out in a steel autoclave equipped with a sparging stirrer. The target product is sampled and characterized at defined intervals using gas chromatography and/or GC-MS (further experimental parameters: $c_{0,hexanal}$=0.04 mol/l in 200 ml of ethanol, $m_{catalyst}$=0.5 g, $U_{stirrer}$=1500 rpm, $P_{H2}$=30 bar and T=40° C.)

Figure 2:
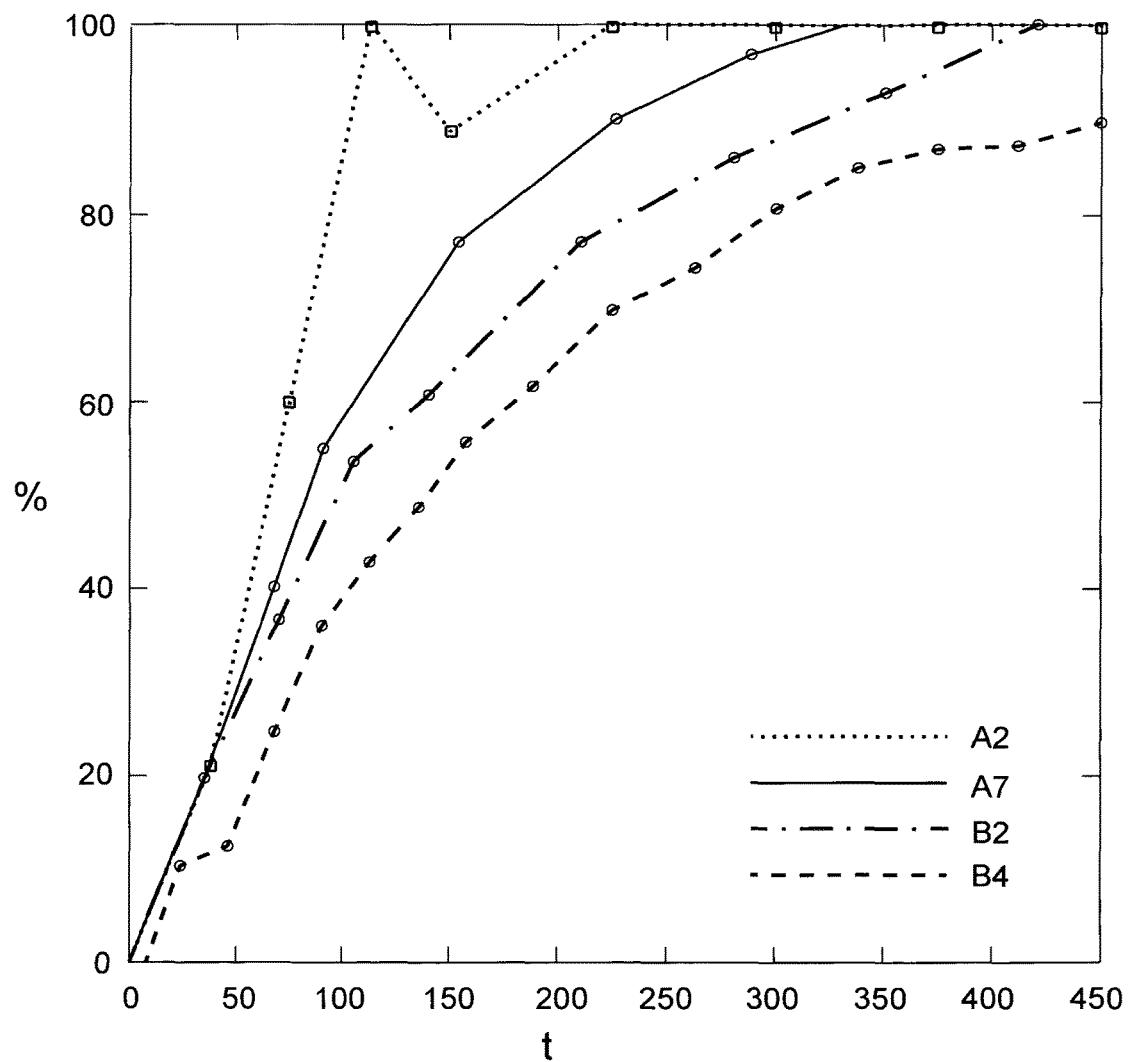

FIG. 2 shows the time course of the formation of hexanol from hexanal for the particular catalyst systems employed. In this case, a faster conversion and/or higher catalytic activity is obtained with inventive catalyst systems A2 and A7, with inventive catalyst system A2 giving the highest conversion and hence the highest catalytic activity. Lower values are found for the (comparative) catalyst system B2, which are minimally greater than those for catalyst system B4. In FIG. 2, the conversion (in %) is reported on the corresponding Y-axis, while the X-axis reports the modified residence time $T_{mod}$, based on the amount of noble metal and total volume.

The investigations reported above demonstrate the conversion enhancement associated with the catalyst systems of the present invention and hence the enhanced catalytic activity of the underlying system in each case, while the best values are found in this context for catalyst system A2, reduced after endowment with the catalytically active component.

3. In a second complex of investigations, the elution resistance of the applied catalytically reactive component and thus the elution stability of the respective catalyst systems was investigated. The catalyst systems employed for this in each case each include the catalytically active component in amounts of 5 wt %, based on the catalyst system. To this end, inventive catalyst system A1 is compared with the non-reduced catalyst system A6 and also with (comparative) catalyst system B1 (non-oxidized activated carbon) and the (comparative) catalyst system D (activated carbon based on coconut shells). To this end, 1 g of each catalyst system under investigation is introduced into an aqueous solution containing hydrochloric acid and also nitric acid (acid content in each case 1 wt %, based on the solution) and left in the solution for 24 hours with stirring. Thereafter, the washed and dried catalyst systems are investigated for their content of catalytically reactive component: while no reduction in the amount of catalytic component was observed for catalyst system A1, a minimal reduction was found for catalyst system A6, the catalyst content following the corresponding elutive/acid treatment having decreased to a value of 4.8 wt %. Catalyst system B1 was found to contain 2.7 wt % of catalytically active component, whereas catalyst system D gave the highest decrease to a value of 1.9 wt %. The respective weights are based on the overall weight of the catalyst system. The present investigations thus show that the catalyst systems of the present invention are particularly elution-resistant systems with firm attachment of the catalytically active component, so only minimal losses of catalytically active component occur in a corresponding elutive treatment and/or in practical service.

4. In a further complex of investigations, the distribution of the catalytically active component in the cross section of the particular catalyst systems employed in the course of this investigation is investigated, the determination in this regard being carried out on the basis of scanning electron microscopy (SEM) studies combined with energy-dispersive X-ray spectroscopy (XDR) for the various catalyst systems. To this end, inventive catalyst systems A1 and also A6 on the one hand and the (comparative) catalyst system B1 and also the reference catalyst system D on the other were compared: while not only inventive catalyst system A1 but also inventive catalyst system A6 were both found to have relatively homogeneous loadings along the radius of the underlying spherical activated carbon with in each case a slight increase in concentration at the exterior (i.e., in the direction of the ball surface), with inventive catalyst system A1 featuring an even more homogeneous distribution than inventive catalyst system A6, a distinctly less homogeneous distribution is obtained for catalyst system B1, although even here it is in principle still ensured that a certain amount of catalytically active component is present even in the interior of the spherical activated carbon. However, the concentration/ amount of catalytically active component in the outer regions of the underlying ball structure is distinctly enhanced. Regarding lastly catalyst system D, a strongly inhomogeneous distribution of the catalytically active component along the radius and/or cross section of the activated carbon is observed here, because the interior of the underlying grain-shaped particle is merely unendowed with the catalytically active component. Ultimately, therefore, the catalyst systems of the present invention comprise distinctly more homogeneous distributions of the catalytically active component in the underlying activated carbon employed as carrier material, entailing a higher/ improved catalytic activity for the respective catalyst systems of the present invention.

The underlying investigations accordingly show altogether in effect that the catalyst systems obtained on the basis of the method according to the present invention have significantly improved properties over those of the prior art.

The invention claimed is:

1. A method of preparing a catalyst system comprising at least one catalytically active component, wherein at least one catalytically active component is fixed on a catalyst carrier, wherein the catalytically active component comprises at least one metal,
wherein said method comprises the following steps in the hereinbelow defined sequence (a) to (d):
(a) providing a spherical activated carbon as a catalyst carrier, wherein the spherical activated carbon is a polymer-based spherical activated carbon, wherein the activated carbon has a Gurvich total pore volume in the range from 0.5 cm$^3$/g to 4 cm$^3$/g, wherein 10% to 85% of the Gurvich total pore volume of the activated carbon is formed by pores having pore diameters in the range from 2 nm to 50 nm, and wherein the activated carbon has a specific BET surface area in the range from 800 m$^2$/g to 3500 m$^2$/g and a particle size in the range from 0.05 mm to 2 mm; then
(b) surface-oxidizing the spherical activated carbon provided in step (a), wherein the surface oxidation of the activated carbon leads to a formation of oxygen-containing functional groups on the surface of the activated carbon, wherein the surface oxidation of the activated carbon is performed via at least one oxidizing agent, wherein the oxidizing agent is selected from the group of hydrogen peroxide, nitric acid and sulfuric acid and their combinations and wherein the oxidizing agent is applied in liquid form in the form of solutions or dispersions, and wherein the surface oxidation is followed by a cleanup via at least one washing operation in a liquid and a drying operation of the oxidized activated carbon; then
(c) providing the surface-oxidized activated carbon of step (b) with at least one catalytically active component to obtain a catalyst system by fixing the catalytically active component on the catalyst carrier; then
(d) reducing the catalyst system obtained in step (c) in the form of the activated carbon endowed with the catalytically active component.

2. The method as claimed in claim 1, wherein the activated carbon has a fractal dimension of open porosity of at least 2.7.

3. The method as claimed in claim 1, wherein the oxygen-containing functional groups are selected from acidic and basic oxygen-containing functional groups and their combinations.

4. The method as claimed in claim 1, wherein the oxygen-containing functional groups are selected from hydroxyl, carboxyl, carbonyl, anhydride, lactone, quinone, pyrone, chromene and ether groups and their combinations.

5. The method as claimed in claim 1, wherein the catalytically active component includes at least one metal in the form of a metal compound or in elemental form.

6. The method as claimed in claim 1, wherein the catalytically active component includes at least one metal selected from the group of Cu, Ag, Au, Zn, Hg, Sn, Ce, Ti, Zr, V, Nb, Cr, Mo, W, Mn, Fe, Bi, Ru, Os, Co, Rh, Re, Ir, Ni, Pd and Pt.

7. The method as claimed in claim 1, wherein the catalytically active component includes at least one metal compound which is soluble or dispersible in an aqueous-based solvent or dispersant medium.

8. The method as claimed in claim 1, wherein the catalytically active component includes at least one metal halide.

9. The method as claimed in claim 1, wherein the catalytically active component includes at least one metal compound selected from the group of palladium chloride, hexachloroplatinic acid, ruthenium chloride, copper chloride, iron chloride, vanadium chloride and lead chloride.

10. The method as claimed in claim 1, wherein the catalytically active component is in the form of an aqueous-based solution or dispersion of the catalytically active component, wherein the solution or dispersion contains the catalytically active component in amounts ranging from 0.01 wt % to 80 wt %, based on the solution or dispersion and reckoned as metal.

11. The method as claimed in claim 1, wherein the step of providing the surface-oxidized activated carbon with the catalytically active component comprises fixing the surface-oxidized activated carbon with the catalytically active component, wherein the fixing is effected by at least one of immersing, wetting, spraying and spray-dispensing the surface-oxidized activated carbon in or with the catalytically active component; and wherein outer and inner surfaces of the surface-oxidized activated carbon are provided with the catalytically active component.

12. The method as claimed in claim 1, wherein the reduction of the catalyst system is effected by using at least one liquid or gaseous reducing agent.

13. The method as claimed in claim 1, wherein the catalyst system includes the catalytically active component in amounts ranging from 0.001 wt % to 30 wt %, reckoned as metal and based on the total weight of the catalyst system.

14. The method as claimed in claim 1, wherein the activated carbon has a Gurvich total pore volume in the range from 0.5 $cm^3/g$ to 3.5 $cm^3/g$, wherein 20% to 80% of the Gurvich total pore volume of the activated carbon is formed by pores having pore diameters in the range from 2 nm to 50 nm.

* * * * *